US009464085B2

(12) United States Patent
Geneste et al.

(10) Patent No.: US 9,464,085 B2
(45) Date of Patent: Oct. 11, 2016

(54) INHIBITOR COMPOUNDS OF PHOSPHODIESTERASE TYPE 10A

(71) Applicants: AbbVie Deutschland GmbH & Co. KG, Wiesbaden (DE); AbbVie Inc., North Chicago, IL (US)

(72) Inventors: Hervé Geneste, Ludwigshafen (DE); Michael Ochse, Ludwigshafen (DE); Karla Drescher, Ludwigshafen (DE); Clarissa Jakob, Abbott Park, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 13/968,242

(22) Filed: Aug. 15, 2013

(65) Prior Publication Data
US 2014/0051695 A1   Feb. 20, 2014

Related U.S. Application Data

(60) Provisional application No. 61/684,290, filed on Aug. 17, 2012.

(51) Int. Cl.
*C07D 471/14* (2006.01)
*C07D 487/04* (2006.01)
*C07D 471/04* (2006.01)

(52) U.S. Cl.
CPC ........... *C07D 471/14* (2013.01); *C07D 471/04* (2013.01); *C07D 487/04* (2013.01)

(58) Field of Classification Search
CPC ... C07D 471/14; C07D 487/04; A61K 31/50
USPC ..................................... 544/234; 514/252.05
See application file for complete search history.

(56) References Cited

U.S. PATENT DOCUMENTS

2007/0155779 A1   7/2007   Verhoest et al.

FOREIGN PATENT DOCUMENTS

| WO | 03/093499 A2 | 11/2003 |
|---|---|---|
| WO | 2005/012485 A2 | 2/2005 |
| WO | 2005/120514 A1 | 12/2005 |
| WO | 2006/028957 A1 | 3/2006 |
| WO | 2007/022280 A1 | 2/2007 |
| WO | 2007/082546 A1 | 7/2007 |
| WO | 2007/085954 A2 | 8/2007 |
| WO | 2007/096743 A1 | 8/2007 |
| WO | 2007/098169 A1 | 8/2007 |
| WO | 2007/098214 A1 | 8/2007 |
| WO | 2007/100880 A1 | 9/2007 |
| WO | 2007/103370 A2 | 9/2007 |
| WO | 2007/103554 A1 | 9/2007 |
| WO | 2007/137819 A1 | 12/2007 |
| WO | 2007/137820 A1 | 12/2007 |
| WO | 2008/001182 A1 | 1/2008 |
| WO | 2008/004117 A1 | 1/2008 |
| WO | 2008/006372 A1 | 1/2008 |
| WO | 2008/020302 A2 | 2/2008 |
| WO | 2009/025823 A1 | 2/2009 |
| WO | 2009/025839 A2 | 2/2009 |
| WO | 2009/029214 A1 | 3/2009 |
| WO | 2009/036766 A1 | 3/2009 |
| WO | 2009/068246 A2 | 6/2009 |
| WO | 2009/068320 A1 | 6/2009 |
| WO | 2009/070583 A1 | 6/2009 |
| WO | 2009/070584 A1 | 6/2009 |

(Continued)

OTHER PUBLICATIONS

Didenko et al., Russian J'nal of Organic Chem. 45(2), 211-214 (2009).*
Brana et al., J. Med. Chem. 2005, 48, 6843-6854 Bogza et al., Chemistry of Heterocyclic Compounds, vol. 40, No. 11, 2004.*
Alkorta et al., Journal of Physical Organic Chemistry J. Phys. Org. Chem. 2005; 18: 719-724.*
Pavlov et al., Chemistry of Heterocyclic Compounds, vol. 40, No. 7, 2004.*

(Continued)

*Primary Examiner* — Paul V Ward
(74) *Attorney, Agent, or Firm* — Lisa V. Mueller; Michael Best & Friedrich LLP

(57) ABSTRACT

The present invention relates to compounds of the formula I, the N-oxides, tautomers, the prodrugs and the pharmaceutically acceptable salts thereof.

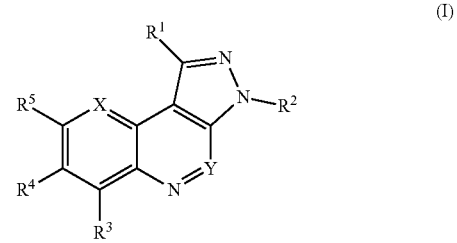

(I)

where in formula I the variables $R^1$, $R^2$, $R^3$, $R^4$ and $R^5$ are as defined in the claims and where X is C—$R^6$ or N, Y is C—$R^7$ or N, where $R^6$ and $R^7$ are, inter alia, hydrogen, halogen, alkoxy, haloalkoxy and the like.

The compounds of the formula I, the N-oxides, tautomers, the prodrugs and the pharmaceutically acceptable salts thereof are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

33 Claims, No Drawings

(56) References Cited

FOREIGN PATENT DOCUMENTS

| WO | 2010/054260 A1 | 5/2010 |
|---|---|---|
| WO | 2011/008597 A1 | 1/2011 |
| WO | 2011/112731 | 9/2011 |
| WO | 2012/000632 | 1/2012 |

OTHER PUBLICATIONS

Ilosokawa, T. et al., "One-pot synthesis of 3-fluoro-4-(trifluoromethyl)quinolines from pentafluoropropen-2-ol and their molecular modification," J. Org. Chem. (2008) 73(4):1468-1474.

Kolotaev, A.V. et al., "Unusual reaction of [alpha]-diketones of the indole series with hydrazine," Russian Chemical Bulletin (2006) 55(5):892-897.

Pavlov, I.V. et al., "Transformations of 5-amino-4-(3,4-dimethoxyphenyl)pyrazoles in the diazotization reaction," Chemistry of Heterocyclic Compounds (2004) 40(7):964-965.

International Search Report and Written Opinion for Application No. PCT/EP2013/067122 dated Jan. 15, 2014.

Schmidt et al, The Journal of Pharmacology and Experimental Therapeutics, 325, 681-690 (2008).

Nishi, The Journal of Neuroscience, 28, 10450-10471 (2008).

Seeger et al., Brain Research, 985, 113-126 (2003).

Rodefer et al., Eur. J. Neurosci., 4, 1070-1076 (2005).

Grauer et al., Journal of Pharmacology and Experimental Therapeutics, fast forward DOI 10.1124 JPET 109.155994 (2009).

Francis et al., Physiol. Rev., 91, 651-690 (2011).

Sotty et al., J. Neurochem., 109, 766-775 (2009).

Cantin et al., Bioorganic & Medicinal Chemistry Letters, 17, 2869-2873 (2007).

Chappie et al., Current Opinion in Drug Discovery & Development, 12(4), 458-467 (2009).

Diaz et al., Journal of Pharmacological and Toxicological Methods, 50, 187-199 (2004).

Bogza et al., Chemistry of Heterocyclic Compounds, 40(11), 1506 (2004).

Siuciak, J.D. et al., "Behavioral and neurochemical characterization of mice deficient in the phosphodiesterase-4B (PDE4B) enzyme," Psychopharm. (2008) 197:115-126.

Blokland, A. et al., "PDE inhibition and cognition enhancement," Exp. Opin. Ther. Patents (2012) 22(4):349-354.

Hoefgen, N. et al., "Targeting PDE10A in schiophrenia," Drugs of the Future (2012) 37(8):577-589.

Kehler, J. et al., "PDE10A inhibitors: novel therapeutic drugs for schizophrenia," Curr. Pharm. Design (2011) 17:137-150.

Kerner, B. et al., "Genome-wide association study in bipolar patients stratified by co-morbidity," PLoS One (2011) 6(12):e28477, 10 pages.

Langen, B. et al., "Effect of PDE10A inhibitors on Mk-801-induced immobility in the forced swim test," Psychopharm. (2011) DOI 10.1007/s00213-011-2567-y.

\* cited by examiner

INHIBITOR COMPOUNDS OF PHOSPHODIESTERASE TYPE 10A

CROSS-REFERENCE TO RELATED APPLICATION(S)

This claims priority of U.S. Provisional Patent Application No. 61/684,290, filed on Aug. 17, 2012.

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126) Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al., Psychopharmacology 2008, 197 (1) 115-126), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-3ly]phenoxymethyl}-quinoline) and TP-10, i.e. 2-{4-[pyridine-4-yl-1-(2,2,2-trifluoroethyl)-1-H-pyrazol-3-3ly]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Imidazo[1,5-a]pyrido[3,2-c]pyridazines and structurally related tricyclic Imidazo[1,5-a]pyridazines—see WO 2007/137819, WO 2007/137820, WO 2009/068246, WO 2009/068320, WO 2009/070583, WO 2009/070584, WO 2010/054260 and WO 2011008597;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214;

MP10 and MP10 like compounds: US 2007/0155779, WO 2008/001182 and WO 2008/004117; and Benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodiesterases such as PDE2, PDE3 or PDE4;
ii. metabolic stability, in particular microsomal stability, e.g. measured in vitro, in liver microsomes from various species (e.g. rat or human) in human cells, such as hepatocytes;
iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
iv. a suitable solubility in water (in mg/ml);
v. suitable pharmacokinetics (time course of the concentration of the compound of the invention in plasma or in tissue, for example brain). The pharmacokinetics can be described by the following parameters: half-life, volume of distribution (in $l·kg^{-1}$), plasma clearance (in $l·h^{-1}·kg^{-1}$), AUC (area under the curve, area under the concentration-time curve (in $ng·h·l^{-1}$), oral bioavailability, (the dose-normalized ratio of AUC after oral administration and AUC after intravenous administration), the so-called brain-plasma ratio (the ratio of AUC in brain tissue and AUC in plasma);
vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).
vii. high free fraction in brain, i.e. the fraction of the compound bound to proteins should be low.
viii. low lipophilicity.

Some tricyclic compounds are commercially available, namely 7,8-dimethoxy-3-benzoyl-1-methyl-3H-2,3,4,5-tetraazacyclopenta[a]naphthalene, 7,8-dimethoxy-3-benzyl-1-methyl-3H-2,3,4,5-tetraazacyclopenta[a]naphthalene, 7,8-dimethoxy-1,3-diphenyl-3H-2,3,4,5-tetraazacyclopenta[a] naphthalene, 7,8-dimethoxy-1-methyl-3H-2,3,4,5-tetraazacyclopenta[a]naphthalene, 7,8-dimethoxy-1-ethyl-3H-2,3,4,5-tetraazacyclopenta[a]naphthalene, 7,8-dimethoxy-1-phenyl-3H-2,3,4,5-tetraazacyclopenta[a] naphthalene, 7,8-dimethoxy-1-benzyl-3H-2,3,4,5-tetraazacyclopenta[a]naphthalene, and 7-methoxy-1-methyl-3H-2,3,4,5-tetraazacyclopenta[a] naphthalene. 7,8-dimethoxy-3-phenyl-1-methyl-3H-2,3,4,5-tetraazacyclopenta[a]naphthalene, (also termed 1-methyl-3-phenyl-7,8-dimethoxy-3H-pyrazolo[3,4-c]cinnoline) has been described by C. L. Bogza et al. in Chemistry of Heterocyclic Compounds, Vol. 40, (2004), 1506.

7,8-Dimethoxy-1-(4-chlorophenyl)-3-(3,5-dichloro-2-pyridyl)-3H-2,3,4,5-tetraazacyclopenta[a]naphthalene (also termed 1-(4-chlorophenyl)-3-(3,5-dichloropyridin-2-yl)-7,8-dimethoxy-3H-pyrazolo[3,4-c]cinnoline) has been described in Chemistry of Heterocyclic Compounds (Translation of Khimiya Geterotsiklicheskikh Soedinenii) (2004), 40(7), 964-965.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal stability, cytosolic stability or hepatocyte stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

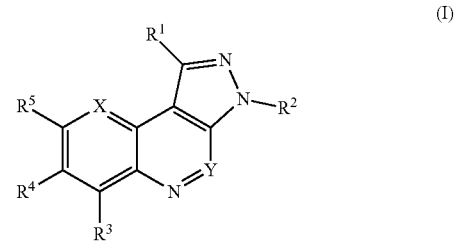

where in formula I the variables X, Y, $R^1$, $R^2$, $R^3$, $R^4$ and $R^5$ have the following meanings:

X is C—$R^6$ or N,
Y is C—$R^7$ or N,
$R^1$ is selected from the group consisting of hydrogen, halogen, cyano, nitro, $R^{11}$, OH, $OR^{12}$, $S(O)_qR^{13}$, C(O)H, $C(O)R^{14}$, C(O)OH, $C(O)OR^{15}$, $OC(O)R^{16}$, $Y^1$—$NR^{17}R^{18}$, $Y^1$—$N(R^{19})$—$Y^3$—$NR^{17}R^{18}$, $Y^1$—N$(R^{19})$—$Y^2$—$R^{15a}$ and a moiety $Z^1$—$Ar^1$;
$R^2$ is selected from the group consisting of $R^{21}$, $OR^{22}$, $C(O)R^{23}$, $C(O)OR^{24}$, $Y^1$—$NR^{25}R^{26}$, $Y^1$—$N(R^{27})$—$Y^3$—$NR^{25}R^{26}$, $Y^1$—N$(R^{27})$—$Y^2$—$R^{28}$ and a moiety $Z^2$—$Ar^2$,
$R^2$ may also be hydrogen, if $R^1$ is different from hydrogen and OH or if $R^3$ is different from hydrogen;

R³ is selected from the group consisting of hydrogen, halogen, cyano, nitro, R³¹, OR³², S(O)$_q$R³³, C(O)H, C(O)R³⁴, C(O)OH, C(O)OR³⁵, OC(O)R³⁶, Y¹—NR³⁷R³⁸, Y¹—N(R³⁹)—Y³—NR³⁷R³⁸ and Y¹—N(R³⁹)—Y²—R³⁵ᵃ, and Z³—Ar³;

R⁴ is selected from the group consisting of hydrogen, halogen, cyano, nitro, R⁴¹, OR⁴², S(O)$_q$R⁴³, C(O)H, C(O)R⁴⁴, C(O)OH, C(O)OR⁴⁵, OC(O)R⁴⁶, Y¹—NR⁴⁷R⁴⁸, Y¹—N(R⁴⁹)—Y³—NR⁴⁷R⁴⁸, Y¹—N(R⁴⁹)—Y²—R⁴⁵ᵃ, and Z⁴—Ar⁴;

R⁵ is selected from the group consisting of hydrogen, halogen, cyano, nitro, R⁵¹, OR⁵², S(O)$_q$R⁵³, C(O)H, C(O)R⁵⁴, C(O)OH, C(O)OR⁵⁵, OC(O)R⁵⁶, Y¹—NR⁵⁷R⁵⁸, Y¹—N(R⁵⁹)—Y³—NR⁵⁷R⁵⁸, Y¹—N(R⁵⁹)—Y²—R⁵⁵ᵃ, and Z⁵—Ar⁵;

or

R⁴ and R⁵, together with the carbon atoms, to which they are attached, may form a fused 5-, 6- or 7-membered carbocyclic or heterocyclic ring, where the fused carbocyclic or heterocyclic ring may be saturated, partially unsaturated or aromatic and where the heterocyclic ring may have 1, 2 or 3 heteroatom moieties as ring members, which are selected from the group consisting of O, N, S, S(O), S(O)₂ or N—Rˣ and where the carbocyclic or heterocyclic ring is unsubstituted or may carry 1, 2, 3 or 4 radicals Rʸʸ;

R⁶ is selected from the group consisting of hydrogen, halogen, cyano, nitro, R⁶¹, OR⁶², S(O)$_q$R⁶³, C(O)H, C(O)R⁶⁴, C(O)OH, C(O)OR⁶⁵, OC(O)R⁶⁶, Y¹—NR⁶⁷R⁶⁸, Y¹—N(R⁶⁹)—Y³—NR⁶⁷R⁶⁸ and Y¹—N(R⁶⁹)—Y²—R⁶⁵ᵃ;

R⁷ is selected from the group consisting of hydrogen, halogen, cyano, nitro, R⁷¹, OR⁷², S(O)$_q$R⁷³, C(O)H, C(O)R⁷⁴, C(O)OH, C(O)OR⁷⁵ and OC(O)R⁷⁶; and a moiety Z⁷—Ar⁷;

R¹¹, R¹², R¹³, R¹⁴, R¹⁵, R¹⁶, R²¹, R²², R²³, R²⁴, R³¹, R³², R³³, R³⁴, R³⁵, R³⁶, R⁴¹, R⁴², R⁴³, R⁴⁴, R⁴⁵, R⁴⁶, R⁵¹, R⁵², R⁵³, R⁵⁴, R⁵⁵, R⁵⁶, R⁶¹, R⁶², R⁶³, R⁶⁴, R⁶⁵, R⁶⁶, R⁷¹, R⁷², R⁷³, R⁷⁴, R⁷⁵ and R⁷⁶, independently of each other, are selected from the group consisting of tri-C₁-C₄-alkylsilyl, C₁-C₈-alkyl, C₂-C₈-alkenyl, C₂-C₈-alkynyl, C₃-C₈-cycloalkyl, C₅-C₈-cycloalkenyl, C₃-C₈-cycloalkyl-C₁-C₄-alkyl, where the 6 aforementioned substituents may be unsubstituted, partially or completely halogenated or carry 1, 2 or 3 radicals Rʸ, and C-bound 5- to 8-membered heterocyclyl, which is saturated or partially unsaturated and has 1 or 2 heteroatom moieties as ring members, which are selected from the group consisting of O, N, S, S(O), S(O)₂ or N—Rˣ, where heterocyclyl is unsubstituted or carries 1, 2, 3 or 4 radicals Rʸʸ;

R¹⁷ and R¹⁸, independently of each other, are selected from the group consisting of tri-C₁-C₄-alkylsilyl, C₁-C₈-alkyl, C₂-C₈-alkenyl, C₂-C₈-alkynyl, C₃-C₈-cycloalkyl, C₅-C₈-cycloalkenyl, C₃-C₈-cycloalkyl-C₁-C₄-alkyl, where the 6 aforementioned substituents may be unsubstituted, partially or completely halogenated or carry 1, 2 or 3 radicals Rʸ, C₁-C₈-alkylcarbonyl, C₁-C₄-haloalkylcarbonyl, C₁-C₈-alkylsulfonyl, C₁-C₄-haloalkylsulfonyl, and C-bound 5- to 8-membered heterocyclyl, which is saturated or partially unsaturated and has 1 or 2 heteroatom moieties as ring members, which are selected from the group consisting of O, N, S, S(O), S(O)₂ or N—Rˣ, where heterocyclyl is unsubstituted or carries 1, 2, 3 or 4 radicals Rʸʸ, or R¹⁷ and R¹⁸ together with the nitrogen atom, to which they are attached, form an N-bound 5- to 8-membered heterocyclyl, which is saturated, partially unsaturated or aromatic and in addition to the nitrogen atom may have 1 or 2 further heteroatom moieties as ring members, which are selected from the group consisting of O, N, S, S(O), S(O)₂ or N—Rˣ, where heterocyclyl is unsubstituted or carries 1, 2, 3 or 4 radicals Rʸʸ;

R¹⁹, R²⁷, R³⁹, R⁴⁹, R⁵⁹ and R⁶⁹, independently of each other, are hydrogen or have one of the meanings given for R¹¹;

R²⁵ and R²⁶ are as defined for R¹⁷ and R¹⁸;
R³⁷ and R³⁸ are as defined for R¹⁷ and R¹⁸;
R⁴⁷ and R⁴⁸ are as defined for R¹⁷ and R¹⁸;
R⁵⁷ and R⁵⁸ are as defined for R¹⁷ and R¹⁸;
R⁶⁷ and R⁶⁸ are as defined for R¹⁷ and R¹⁸;

R¹⁵ᵃ, R²⁸, R³⁵ᵃ, R⁴⁵ᵃ, R⁵⁵ᵃ and R⁶⁵ᵃ, independently of each other, have one of the meanings given for R¹¹;

q is 0, 1 or 2

Ar¹, Ar², Ar³, Ar⁴, Ar⁵, Ar⁶ and Ar⁷, independently of each other, are selected from the group consisting of aryl, monocyclic 5- or 6-membered hetaryl and bicyclic 9 or 10 membered hetaryl, where hetaryl has 1, 2 or 3 heteroatoms as ring members which are selected from O, S and N, where aryl and hetaryl are unsubstituted or may carry 1, 2, 3 or 4 identical or different substituents $R^{Ar}$;

Y¹ is a single bond, C₁-C₄-alkylene, Y⁵—O—Y⁶, Y⁵—S(O)$_q$—Y⁶, Y⁵—C(O)—Y⁶, Y⁵—C(S)—Y⁶, Y⁵—C(O)O—Y⁶, Y⁵—OC(O)—Y⁶, or Y⁵—N(Rᶻ)—Y⁴;

Y² is a single bond, C₁-C₄-alkylene, Y⁵—O—Y⁶, Y⁵—S(O)$_q$—Y⁶, Y⁵—C(O)—Y⁶, Y⁵—C(S)—Y⁶, Y⁵—C(O)O—Y⁶, Y⁵—OC(O)—Y⁶, or Y⁵—N(Rᶻ)—Y⁴;

Y³ is a single bond, C₁-C₄-alkylene, Y⁵—S(O)$_q$—Y⁶, Y⁵—C(O)—Y⁶, Y⁵—C(S)—Y⁶, Y⁵—C(O)O—Y⁶, or Y⁵—OC(O)—Y⁶;

Y⁴ is a C₁-C₄-alkylene, Y⁵—S(O)$_q$—Y⁶, Y⁵—C(O)—Y⁶, Y⁵—C(S)—Y⁶, Y⁵—C(O)O—Y⁶, or Y⁵—OC(O)—Y⁶;

Y⁵ is a single bond or C₁-C₄-alkylene;
Y⁶ is a single bond or C₁-C₄-alkylene;

Z¹ is a single bond, C₁-C₄-alkylene, Y⁵—O—Y⁶, Y⁵—S(O)$_q$—Y⁶, Y⁵—C(O)—Y⁶, Y⁵—C(S)—Y⁶, Y⁵—C(O)O—Y⁶, Y⁵—OC(O)—Y⁶, or Y⁵—N(Rᶻ)—Y⁴;

Z² is a single bond, C₁-C₄-alkylene, Y⁵—O—Y⁶, Y⁵—C(O)—Y⁶, Y⁵—C(S)—Y⁶, Y⁵—C(O)O—Y⁶, Y⁵—OC(O)—Y⁶, or Y⁵—N(Rᶻ)—Y⁴;

Z³, Z⁴, Z⁵, Z⁶ and Z⁷ are independently of each other selected from the group consisting of a single bond, C₁-C₄-alkylene, Y⁵—O—Y⁶, Y⁵—S(O)$_q$—Y⁶, Y⁵—C(O)—Y⁶, Y⁵—C(S)—Y⁶, Y⁵—C(O)O—Y⁶, Y⁵—OC(O)—Y⁶ and Y⁵—N(Rᶻ)—Y⁴;

Rˣ is selected from the group consisting of hydrogen, C₁-C₈-alkyl, C₂-C₈-alkenyl, C₂-C₈-alkynyl, C₃-C₈-cycloalkyl, C₅-C₈-cycloalkenyl, C₃-C₈-cycloalkyl-C₁-C₄-alkyl, where the 6 aforementioned substituents may be unsubstituted, partially or completely halogenated or carry 1, 2 or 3 radicals Rʸ, phenyl and phenyl-C₁-C₄-alkyl, where phenyl and phenyl-C₁-C₄-alkyl are unsubstituted or may carry 1, 2, 3 or 4 radicals Rʸʸ;

Rʸ is selected from the group consisting of cyano, OH, C₁-C₄-alkyl, C₁-C₄-haloalkyl, ORʸ², S(O)$_q$Rʸ³, C(O)H, C(O)Rʸ⁴, C(O)OH, C(O)ORʸ⁵, OC(O)Rʸ⁶, Y¹—NRʸ⁷Rʸ⁸, Y¹—N(Rʸ⁹)—Y³—NRʸ⁷Rʸ⁸ and Y¹—N(Rʸ⁹)—Y²—Rʸ⁰;

Rʸʸ is selected from the group consisting of cyano, halogen, Rʸ¹, OH, ORʸ², S(O)$_q$Rʸ³, C(O)H, C(O)Rʸ⁴, C(O)OH, C(O)ORʸ⁵, OC(O)Rʸ⁶, Y¹—NRʸ⁷Rʸ⁸, Y¹—N(Rʸ⁹)—Y³—NRʸ⁷Rʸ⁸ and Y¹—N(Rʸ⁹)—Y²—Rʸ⁰;

Rʸ⁰, Rʸ¹, Rʸ², Rʸ³, Rʸ⁴, Rʸ⁵ and Rʸ⁶, independently of each other, are selected from the group consisting of C₁-C₈-alkyl, C₂-C₈-alkenyl, C₂-C₈-alkynyl, C₃-C₈-cycloalkyl, C₅-C₈-cycloalkenyl, C₃-C₈-cycloalkyl-C₁-C₄-alkyl, and C-bound 5- to 8-membered heterocyclyl, which is saturated or partially unsaturated and has 1 or 2 heteroatom moieties as ring members, which are selected from the group consisting of O, N, S, S(O), S(O)$_2$, NH or N—(C$_1$-C$_4$-alkyl);

R$^{y7}$ and R$^{y8}$ are as defined for R$^{y0}$ or, together with the nitrogen atom, to which they are attached, form an N-bound 5- to 8-membered heterocyclyl, which is saturated or partially unsaturated and in addition to the nitrogen atom may have 1 or 2 further heteroatom moieties as ring members, which are selected from the group consisting of O, N, S, S(O), S(O)$_2$, NH or N—(C$_1$-C$_4$-alkyl), where heterocyclyl is unsubstituted or carries 1, 2, 3 or 4 radicals selected from C$_1$-C$_4$-alkyl;

R$^{y9}$ is hydrogen or has one of the meanings given for R$^{y0}$;

R$^{4r}$ is selected from the group consisting of halogen, cyano, nitro, OH, C(O)NH$_2$, R$^{Ar1}$, OR$^{Ar2}$, S(O)$_q$R$^{Ar3}$, C(O)H, C(O)R$^{Ar4}$, C(O)OH, C(O)OR$^{Ar5}$, OC(O)R$^{Ar6}$, Y$^1$—NR$^{Ar7}$R$^{Ar8}$, Y$^1$—N(R$^{Ar9}$)—Y$^3$—NR$^{Ar7}$R$^{Ar8}$, Y$^1$—N(R$^{Ar9}$)—Y$^2$—R$^{Ar0}$, where R$^{Ar0}$, R$^{Ar1}$, R$^{Ar2}$, R$^{Ar3}$, R$^{Ar4}$, R$^{Ar5}$ and R$^{Ar6}$ have one of the meanings given for R$^{11}$ or may be phenyl, R$^{Ar7}$ and R$^{Ar8}$ are as defined for R$^{17}$ and R$^{18}$, and R$^{Ar9}$ has one of the meanings given for R$^{19}$; and R$^z$ has one of the meanings given for R$^x$.

Therefore, the present invention relates to the compounds of formula I as described herein and, the N-oxides, the prodrugs, the hydrates and the tautomers thereof and the pharmaceutically suitable salts thereof, except for the compounds of the formula I belonging to the following groups a), b), c) and d), where group a): compounds of the formula I, where X is CH, Y is N, R$^1$ is methyl, R$^2$ is hydrogen, phenyl, benzyl or benzoyl, R$^3$ is hydrogen, R$^4$ and R$^5$ are methoxy, and the pharmaceutically acceptable salts thereof group b): compounds of the formula I, where X is CH, Y is N, R$^1$ is phenyl, R$^2$ is phenyl, R$^3$ is hydrogen, R$^4$ and R$^5$ are methoxy, and the pharmaceutically acceptable salts thereof;

group c): compounds of the formula I, where X is CH, Y is N, R$^1$ is 4-chlorophenyl, R$^2$ is 3,5-dichloro-2-pyridyl, R$^3$ is hydrogen, R$^4$ and R$^5$ are methoxy, and pharmaceutically acceptable salts thereof group d): compounds of the formula I, where X is CH, Y is N, R$^1$ is methyl, ethyl. benzyl or phenyl, R$^2$ is hydrogen, R$^3$ is hydrogen, R$^4$ and R$^5$ are both methoxy and the compound of the formula I, where X is CH, Y is N, R$^1$ is methyl, R$^2$ is hydrogen, R$^3$ is hydrogen, R$^4$ is methoxy and R$^5$ is hydrogen, and the pharmaceutically acceptable salts thereof.

The present invention therefore relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I. The present invention in particular relates to the compounds of the general formula I and to their pharmaceutically acceptable salts.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of a medical disorder, selected from neurological and psychiatric disorders which can be treated by modulation of phosphodiesterase type 10.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates effectively inhibit PDE10A even at low concentrations. They are additionally distinguished by a high selectivity in relation to the inhibition of the PDE10A vis-à-vis inhibition of other phosphodiesterase, such as PDE2, PDE3 or PDE4. The compounds of the invention may additionally have one or more of the above mentioned properties ii. to viii.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates are therefore particularly suitable for treating disorders and conditions in creatures, especially human creatures, which can be treated or controlled by inhibition of phosphodiesterase type 10A.

The invention therefore also relates to the use of the compounds of the formula I, their N-oxides, their tautomers, their hydrates and their pharmaceutically acceptable salts and the pharmaceutically acceptable salts of said N-oxides, prodrugs, tautomers or hydrates for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or an N-oxide, a tautomer, or a hydrate or a prodrug of said compound I, or a pharmaceutically acceptable salt of the compound of the formula I or a pharmaceutically acceptable salt of the N-oxide, the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or NH$_2$-group, where the OH or NH$_2$-group forms an ester/amide/peptide linkage, i.e. where one of the hydrogen atoms of the OH or NH$_2$-group is substituted by a C$_1$-C$_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or NH$_2$-group via the carbonyl group of the amino acid. Further suitable prodrugs are alkylcarbonyloxyalkyl carbonates or carbamates of compounds I carrying an OH- or NH$_2$-group in which one of the hydrogen atoms of the OH- or NH$_2$-group has been replaced by a group of the formula —C(═O)—O—CHR$^p$—O—C(═O)—R$^q$ in which R$^p$ and R$^q$ are independently of one another C$_1$-C$_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug, tautomer, hydrate or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug, tautomer, hydrate or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de >90%). The compounds are preferably in the form of essentially diastereomerically pure compounds (diastereomeric excess de >90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee >90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

The present invention moreover relates to compounds as defined herein, wherein one or more of the atoms depicted in formula I have been replaced by a stable isotope (e.g., hydrogen by deuterium, $^{12}C$ by $^{13}C$, $^{14}N$ by $^{15}N$, $^{16}O$ by $^{18}O$) or by an instable isotope (e.g. $^{12}C$ by $^{11}C$, $^{16}O$ by $^{15}O$, $^{19}F$ by $^{18}F$), preferably by a stable isotope, or enriched with regard to said isotope beyond the natural level. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkynyl", "alkoxy", "alkenyloxy", "haloalkyl", "haloalkoxy", "cycloalkyl", "halogenated cycloalkyl", "cycloalkenyl", "halogenated cycloalkenyl", "alkylene", "alkandiyl", "heterocyclyl", "hetaryl", "aryl" and radicals derived therefrom, such as "hydroxylalkyl", "alkoxylalkyl", "alkoxyalkoxy", "cycloalkylalkyl", "halogenated cycloalkylalkyl" and "hetarylalkyl" represent groups of individual radicals. The groups of noncyclic radicals "alkyl", "alkenyl", "alkynyl", "alkoxy", "haloalkyl", "haloalkoxy", "alkylene", "alkandiyl", and the groups of radicals derived therefrom always include both unbranched and branched "alkyl", "alkenyl", "alkynyl", "alkoxy", "haloalkyl", "haloalkoxy", "alkylene" and "alkandiyl", respectively.

The prefix $C_n$-$C_m$- indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine The term "partially or completely halogenated" indicates that at least on, e.g. 1, 2, 3, 4, 5 or 6 of the hydrogen atoms or all of the hydrogen atoms of the respective moiety are replaced by halogen atoms, in particular by fluorine atoms Examples of other meanings are:

Alkyl, and the alkyl moieties for example in alkylcarbonyl, alkylsulfanyl, alkylsulfonyl, alkylsulfanylalkyl and alkylsulfaylalkoxy: saturated, straight-chain or branched hydrocarbon radicals having one or more C atoms, e.g. 1 to 10, 1 to 8, 1 to 6 or 1 to 4 carbon atoms. Examples of $C_1$-$C_4$-alkyl are methyl, ethyl, propyl, 1-methylethyl, n-butyl, 1-methylpropyl, 2-methylpropyl and 1,1-dimethylethyl. $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples for $C_1$-$C_8$-alkyl or $C_2$-$C_{10}$-alkyl are, apart those mentioned for $C_1$-$C_6$-alkyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl and 1-propylpentyl, 2-propylpentyl.

Haloalkyl and the Haloalkyl moieties for example in haloalkylsulfonyl: an alkyl radical having ordinarily 1 to 4

C atoms, in particular 1 or 2 C-atoms ($C_1$-$C_2$-fluoroalkyl) as mentioned above, whose hydrogen atoms are partly or completely replaced by halogen atoms, in particular by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy, cycloalkyl-$C_1$-$C_4$-alkyl or cycloalkyl-$C_1$-$C_4$-alkoxy: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl.

Halogenated cycloalkyl, and the halogenated cycloalkyl moieties for example in halogenated cycloalkoxy or halogenated cycloalkyl-$C_1$-$C_4$-alkyl: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl, wherein at least one, e.g. 1, 2, 3, 4, 5 or 6 or all of the hydrogen atoms are replaced by halogen atoms, in particular by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkenyl: a mono-unsaturated monocyclic hydrocarbon groups having 5- or more C atoms, e.g. 5, 6, 7 or 8 carbon ring members, such as 1-cyclopenten-1-yl, 3-cyclopenten-1-yl, 4-cyclopenten-1-yl, 1-cyclohexen-1-yl, 3-cyclohexen-1-yl, 4-cyclohexen-1-yl, 1-cyclohepten-1-yl, 3-cyclohepten-1-yl, 4-cyclohepten-1-yl, 5-cyclohepten-1-yl, 1-cycloocten-1-yl, 2-cycloocten-1-yl, 3-cycloocten-1-yl, 4-cycloocten-1-yl and 5-cycloocten-1-yl.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl, cyclohexylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl or 2-cyclohexylethyl.

Halogenated cycloalkylalkyl: a halogenated, in particular a fluorinated cycloalkyl radical as defined above which is linked via an alkylene group, in particular via a methylene, 1,1-ethylene or 1,2-ethylene group, e.g. 1-fluorocyclopropylmethyl, 2-fluorocyclopropylmethyl, 2,2-difluorocyclopropylmethyl, 1,2-difluorocyclopropylmethyl, 2,3-difluorocyclopropylmethyl, 1-(1-fluorocyclopropyl)ethyl, 1-(2-fluorocyclopropyl)ethyl, 1-(2,2-difluorocyclopropyl)ethyl, 1-(1,2-difluorocyclopropyl)ethyl, 1-(2,3-difluorocyclopropyl)ethyl, 2-(1-fluorocyclopropyl)ethyl, 2-(2-fluorocyclopropyl)ethyl, 2-(2,2-difluorocyclopropyl)ethyl, 2-(1,2-difluorocyclopropyl)ethyl or 2-(2,3-difluorocyclopropyl)ethyl.

Alkenyl, and alkenyl moieties for example in alkenyloxy: monounsaturated, straight-chain or branched hydrocarbon radicals having two or more C atoms, e.g. 2 to 8, especially 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkynyl, and alkenyl moieties for example in alkynyloxy: monounsaturated, straight-chain or branched hydrocarbon radicals having two or more C atoms, e.g., e.g. 2 to 8, especially 2 to 6 carbon atoms and one C≡C-triple bond in any position, e.g. $C_2$-$C_4$-alkenyl such as ethynyl, 1-propynyl, 2-propynyl, 1-butynyl, 2-butynyl, 3-butynyl, 1-methyl-2-propynyl, 1-methyl-2-butynyl and 2-methyl-3-butynyl.

Alkoxy or alkoxy moieties for example in alkoxyalkyl and alkoxyalkoxy:

an alkyl radical as defined above having preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Haloalkoxy: alkoxy as described above, in which the hydrogen atoms of these groups are partly or completely replaced by halogen atoms, in particular by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyethyl, 1-methyl-1-hydroxypropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethyl-ethoxy)ethoxy, etc.

"Alkylen" or "Alkandiyl", respectively: a saturated hydrocarbon chain having ordinarily from 1 to 4 carbon atoms, such as methylen (—$CH_2$—), 1,2-ethylen (—$CH_2CH_2$—), 1,1-ethandiyl (—$CH(CH_3)$—), 1,2-propandiyl, 1,3-propandiyl, 1,4-butandiyl, 1,2-butandiyl, 1,3-butandiyl, 1-methyl-1,2-propandiyl, 2-methyl-1,3-propandiyl, 1-methyl-1,1-ethandiyl, 1-methyl-1,2-propandiyl etc.

Aryl: an monocyclic or fused bi- or tricyclic carbocyclic radical having at least one, e.g. 1, 2 or 3 fused phenyl rings, or one or two fused phenyl rings and 1 or two fused saturated carbocyclic rings, examples being phenyl, naphthyl, fluorenyl, indanyl, and indenyl.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:
Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:
C-bonded, 3- or 4-membered saturated rings such as 2-oxiranyl, 2-oxetanyl, 3-oxetanyl, 2-aziridinyl, 3-thietanyl, 1-azetidinyl, 2-azetidinyl.
C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.
C-bonded, 6-membered saturated rings such as:
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyridazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.
N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.
N-bonded, 6-membered saturated rings such as:
piperidin-1-yl, hexahydropyrimidin-1-yl, hexahydropyridazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:
C-bonded, 5-membered, partially unsaturated rings such as:
2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.
C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetra-hydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetra-hydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydro-pyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4- dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8-, 9- or 10-membered aromatic heterobicyclic radical (also termed 8-, 9- or 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

bicyclic 8-, 9-10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2NH$-phenyl, $SO_2$-phenyl, NH—$SO_2$-phenyl, NH—CO-phenyl, CONH-hetaryl, $SO_2NH$-hetaryl, NH—$SO_2$-hetaryl and NH—CO-hetaryl, where hetaryl in the for last mentioned radicals is 5- or 6-membered hetaryl having one heteroatom selected from O, S and N as ring member and optionally one further nitrogen atom as ring member, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as inhibitors of PDE10A, the variables X, Y, $R^1$, $R^2$, $R^3$, $R^4$ and $R^5$ in formula I preferably have the following meanings, where these represent, both considered on their own and in combination with at least one other or all, special embodiments of the compounds of the formula I:

A particular group of embodiments relates to compounds of the formula I, where X is C—$R^6$. In this embodiment, $R^6$ is as defined above. Frequently $R^6$ is selected from the group consisting of hydrogen, halogen, $C_1$-$C_4$-alkyl, $C_1$-$C_4$-alkoxy, $C_1$-$C_2$-haloalkyl and $C_1$-$C_2$-haloalkoxy, in particular selected from the group consisting of hydrogen, halogen, methyl, methoxy, $CHF_2$, $CF_3$, $OCHF_2$ or $OCF_3$, and especially $R^6$ is hydrogen.

Another particular group of embodiments relates to compounds of the formula I, where X is N.

A further particular group of embodiments relates to compounds of the formula I, where Y is N.

Another further particular group of embodiments relates to compounds of the formula I, where Y is C—$R^7$. In this embodiment, $R^7$ is as defined above. Frequently $R^7$ is selected from the group consisting of hydrogen, halogen, CN, $C_1$-$C_4$-alkyl, $C_1$-$C_4$-alkoxy, $C_3$-$C_6$-cycloalkoxy, $S(O)_q$—$C_1$-$C_4$-alkyl, $S(O)_q$—$C_1$-$C_4$-haloalkyl (q=0, 1 or 2) $C_1$-$C_2$-haloalkyl, $C_1$-$C_2$-haloalkoxy and the moiety $Z^7$—$Ar^7$. In this group of embodiments, $R^7$ is in particular selected from the group consisting of hydrogen, halogen, methyl, methoxy, CN, $CHF_2$, $CF_3$, $OCHF_2$ or $OCF_3$, and especially $R^7$ is hydrogen, methyl, fluorine or chlorine. In this group of embodiments, $R^7$ may also be a radical $NR^{77}R^{78}$, where $R^{77}$ and $R^{78}$ are as defined herein and where $R^{77}$ and $R^{78}$ in particular are independently of each other selected from the group consisting of hydrogen, $C_1$-$C_4$-alkyl, $C_3$-$C_6$-cycloalkyl, $C_1$-$C_8$-alkylcarbonyl, $C_1$-$C_4$-haloalkylcarbonyl, $C_1$-$C_8$-alkylsulfonyl, $C_1$-$C_4$-haloalkylsulfonyl or $R^{77}$ and $R^{78}$, together with the nitrogen atom, to which they are attached, form an N-bound 5-, 6- or 7-membered heterocyclyl, which is saturated or aromatic and in addition to the nitrogen atom may have 1 or 2 further heteroatom moieties as ring members, which are selected from the group consisting of O, N, S or N—$R^x$, where heterocyclyl is unsubstituted or carries 1, 2, 3 or 4 radicals $R^{yy}$; and where the moiety $NR^{77}R^{78}$, is in particular selected from $NH_2$, $NHSO_2$—$C_1$-$C_4$-alkyl, morpholine-4-yl, piperidine-1-yl, piperazine-1-yl, 1H-imidazole-1-yl or NH—$C_3$-$C_6$-cycloalkyl.

In the embodiments where Y is C—$R^7$ and $R^7$ is a moiety $Z^7$—$Ar^7$ the variable $Z^7$ is in particular selected from the group consisting of O, $CH_2$, $CH_2CH_2$, $OCH_2$, $OCH_2CH_2$, $CH_2O$, $CH_2CH_2O$, $CH_2S$ and $SCH_2$. In these embodiments, $Ar^7$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^7$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^7$ radical has at least one imino-nitrogen as ring member, which is located in the position adjacent to carbon atom bound to the group $Z^7$. Amongst these, particular preference is given to those, where $Ar^7$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^7$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

Compounds or the formula I, where X is C—$R^6$ and Y is N are hereinafter termed as compounds of the formula I-A or compounds I-A, respectively.

Compounds or the formula I, where X is N and Y is N are hereinafter termed as compounds of the formula I-B or compounds I-B, respectively.

Compounds or the formula I, where X is C—$R^6$ and Y is C—$R^7$ are hereinafter termed as compounds of the formula I-C or compounds I-C, respectively.

Compounds or the formula I, where X is N and Y is C—$R^7$ are hereinafter termed as compounds of the formula I-D or compounds I-D, respectively.

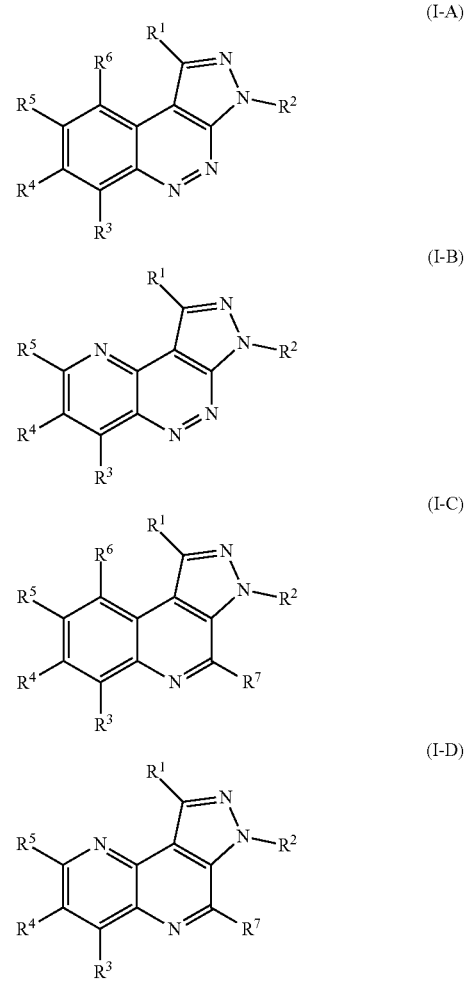

In formulae I-A, I-B, I-C and I-D, the variables $R^1$, $R^2$, $R^3$, $R^4$, $R^5$, $R^6$ and $R^7$ are as defined above or hereinafter.

Preferably, $R^1$ in formulae I, I-A, I-B, I-C and I-D is different from hydrogen. In a particular group of embodiments, the variable $R^1$ in formulae I, I-A, I-B, I-C and I-D is a radical $R^{11}$ or a moiety $Z^1$—$Ar^1$, where $R^{11}$, $Z^1$ and $Ar^1$ are as defined above.

In this particular group of embodiments, the variable $R^{11}$, is in particular selected from the group consisting of tri-$C_1$-$C_4$-alkylsilyl, $C_1$-$C_8$-alkyl, $C_3$-$C_8$-cycloalkyl and $C_3$-$C_8$-cycloalkyl-$C_1$-$C_4$-alkyl, where the 3 aforementioned substituents may be unsubstituted, partially or completely fluorinated or carry 1, 2 or 3 radicals $R^y$, and C-bound 5- to 8-membered heterocyclyl, which is saturated and has 1 or 2 heteroatom moieties as ring members, which are selected from the group consisting of O, S, $SO_2$ and N—$R^x$, where heterocyclyl is unsubstituted or carries 1, 2, 3 or 4 radicals $R^{yy}$.

In this context, $R^y$ is in particular selected from the group consisting of OH, CN, $C_1$-$C_4$-alkoxy, especially methoxy, and $C_1$-$C_4$-hydroxyalkoxy, especially 2-hydroxyethoxy. In this context, $R^x$ is in particular selected from the group consisting of hydrogen and $C_1$-$C_4$-alkyl, especially methyl.

In this context, $R^{yy}$ is in particular selected from the group consisting of halogen, especially fluorine, $C_1$-$C_4$-alkyl, especially methyl, $C_1$-$C_4$-alkoxy, especially methoxy, $C_1$-$C_2$- fluoroalkyl such as difluoromethyl or trifluoromethyl, and $C_1$-$C_2$-fluoroalkoxy such as difluoromethoxy or trifluoromethoxy.

In this particular group of embodiments, the variable $R^{11}$ is especially selected from the group consisting of $C_1$-$C_8$-alkyl, $C_3$-$C_8$-cycloalkyl, such as cyclopropyl, cyclobutyl, cyclopentyl and cyclohexyl and $C_3$-$C_8$-cycloalkyl-$C_1$-$C_4$-alkyl such as cyclopropylmethyl, cyclobutylmethyl and cyclopentylmethyl and cyclohexyl, where the cycloalkyl moieties in the aforementioned radicals are unsubstituted or carry 1, 2 or 3 radicals selected from fluorine and methyl.

In this particular group of embodiments, the variable $Z^1$, is in particular selected from a single bond, O, $CH_2$, $CH_2CH_2$, $CH_2O$ and $OCH_2$, especially $Z^1$ is a single bond.

In this particular group of embodiments, the variable $Ar^1$, is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents $R^{Ar}$. In this particular group of embodiments, the variable $Ar^1$, is in especially selected from the group consisting of phenyl, thienyl, pyrazolyl, isoxazolyl, thiazolyl and pyridyl, where phenyl, thienyl, pyrazolyl, isoxazolyl, thiazolyl and pyridyl are unsubstituted or carry 1, 2, 3 or 4 identical or different substituents $R^{Ar}$.

In a special group of embodiments, the variable $R^1$ is a radical $Ar^1$, i.e. $Z^1$ is a single bond. In this special group of embodiments, $Ar^1$ is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents $R^{Ar}$. In this special group of embodiments, the variable $Ar^1$, is in especially selected from the group consisting of phenyl, thienyl, pyrazolyl, isoxazolyl, thiazolyl, 1,2,4-oxadiazolyl and pyridyl, where phenyl, thienyl, pyrazolyl, isoxazolyl, thiazolyl, 1,2,4-oxadiazolyl and pyridyl are unsubstituted or carry 1, 2, 3 or 4 identical or different substituents $R^{Ar}$.

In this context, $R^{Ar}$ is preferably selected from the group consisting of halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—$(C_1$-$C_6$-alkyl$)_2$, $SO_2N$—$(C_1$-$C_6$-alkyl$)_2$, NH—$SO_2$—$C_1$-$C_4$-alkyl, NH—$SO_2$—$C_1$-$C_4$-haloalkyl, NH—CO—$C_1$-$C_4$-alkyl, NH—CO—$C_1$-$C_4$-haloalkyl, $SO_2$—$C_1$-$C_4$-alkyl, $SO_2$—$C_1$-$C_6$-haloalkyl, phenyl, O-phenyl, O—$CH_2$-phenyl, CONH-phenyl, $SO_2NH$-phenyl, $SO_2$-phenyl, NH—$SO_2$-phenyl, NH—CO-phenyl, CONH-hetaryl, $SO_2NH$-hetaryl, NH—$SO_2$-hetaryl and NH—CO-hetaryl, where hetaryl in the for last mentioned radicals is 5- or 6-membered hetaryl having one heteroatom selected from O, S and N as ring member and optionally one further nitrogen atom as ring member, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy. In this context, $R^{Ar}$ is preferably selected from the group consisting of halogen, especially fluorine or chlorine, $C_1$-$C_4$-alkyl, especially methyl, $C_1$-$C_4$-alkoxy, especially methoxy, $C_1$-$C_2$-fluoroalkyl such as difluoromethyl or trifluoromethyl, and $C_1$-$C_2$-fluoroalkoxy such as difluoromethoxy or trifluoromethoxy.

In another particular group of embodiments, the variable $R^1$ in formulae I, I-A, I-B, I-C and I-D is CN or a moiety $Y^1$—$NR^{17}R^{18}$, where $R^{17}$, $R^{18}$ and $Y^1$ are as defined herein. In particular $Y^1$ is C=O.

Preferably, $R^2$ in formulae I, I-A, I-B, I-C and I-D is different from hydrogen. In a particular group of embodiments, the variable $R^2$ in formulae I, I-A, I-B, I-C and I-D is a radical $R^{21}$ where $R^{21}$ is as defined above. In particular, $R^2$ (and likewise $R^{21}$) is selected from the group consisting of trimethylsilyl, $C_1$-$C_8$-alkyl, $C_3$-$C_8$-cycloalkyl and $C_3$-$C_8$-cycloalkyl-$C_1$-$C_4$-alkyl, where the three last mentioned radicals may be unsubstituted, partially or completely halogenated or where the $C_3$-$C_8$-cycloalkyl radicals may carry 1, 2 or 3 radicals $R^{y'}$, where $R^{y'}$ has one of the meanings given for $R^y$, and where $R^{y'}$ is in particular selected from the group consisting of halogen, especially fluorine, $C_1$-$C_4$-alkyl, especially methyl, $C_1$-$C_4$-alkoxy, especially methoxy, $C_1$-$C_2$-fluoroalkyl, especially difluoromethyl or trifluoromethyl, $C_1$-$C_2$-fluoroalkoxy, especially difluoromethoxy or trifluoromethoxy, and where $R^{y'}$ is especially methyl. In this particular group of embodiments $R^2$ is more particularly $C_1$-$C_4$-alkyl, such as methyl or ethyl, $C_1$-$C_2$-alkoxy-$C_1$-$C_2$-alkyl such as methoxymethyl, $C_1$-$C_2$-alkylamino-$C_1$-$C_2$-alkyl, such as methylaminomethyl, or $C_1$-$C_2$-fluoroalkyl, especially difluoromethyl or trifluoromethyl. $R^2$ is especially methyl.

In one embodiment, $R^2$ is different from a group $Z^2$—$Ar^2$.

In another embodiment, $R^2$ is a group $Z^2$—$Ar^2$. In this embodiment $Z^2$ is in particular a single bond. In this special group of embodiments, $Ar^2$ is in particular selected from phenyl and 5- or 6-membered hetaryl having one heteroatom as ring member, which is selected from O, S and N, and optionally one further nitrogen atom as ring member, where phenyl and 5- or 6-membered hetaryl are unsubstituted or carry 1, 2, 3 or 4 identical or different substituents $R^{Ar}$. In this special group of embodiments, the variable $Ar^2$, is in especially selected from the group consisting of phenyl, thienyl, pyrazolyl, isoxazolyl, thiazolyl and pyridyl, where phenyl, thienyl, pyrazolyl, isoxazolyl, thiazolyl and pyridyl are unsubstituted or carry 1, 2, 3 or 4 identical or different substituents $R^{Ar}$. As regards preferred meanings of $R^{Ar}$, reference is made to the preferred and particular meanings of $R^{Ar}$ given above in context with $Ar^1$.

In particular, one or two of the radicals $R^3$, $R^4$ and $R^5$ in formulae I, I-A, I-B, I-C and I-D are different from hydrogen. More particularly $R^5$ is different from hydrogen. In particular one of $R^3$ and $R^4$ is different from hydrogen. In particular $R^5$ is different form hydrogen and one of $R^3$ and $R^4$ is different from hydrogen. In particular $R^3$ is different from hydrogen. Especially, $R^3$ and $R^5$ are different form hydrogen while $R^4$ is hydrogen.

Particularly, at most one of the radicals $R^3$, $R^4$ and $R^5$ and especially none of the radicals $R^3$, $R^4$ and $R^5$ are a radical $Z^3$—$Ar^3$, $Z^4$—$Ar^4$, and $Z^5$—$Ar^5$, respectively.

If $R^3$ is different from hydrogen, $R^3$ is in particular halogen, especially fluorine, or a radical $OR^{32}$, where $R^{32}$ is as defined above, and where $R^{32}$ is in particular $C_1$-$C_4$-alkyl, such as methyl, or $C_1$-$C_4$-haloalkyl, especially $C_1$-$C_2$-fluoroalkyl, such as difluoromethyl, trifluoromethyl, 2,2-difluoroethyl or 2,2,2-trifluoroethyl.

In particular, $R^3$ is selected from the group consisting of hydrogen, halogen, especially fluorine and $OR^{32}$, where $R^{32}$ is as defined above. $R^3$ is in particular hydrogen, $C_1$-$C_4$-alkoxy or $C_1$-$C_4$-haloalkoxy. $R^3$ is especially $C_1$-$C_4$-alkoxy or $C_1$-$C_2$-fluoroalkoxy and more especially $R^3$ is methoxy difluoromethoxy, trifluoromethoxy, 2,2-difluoroethoxy or 2,2,2-trifluoroethoxy and most especially $R^3$ is methoxy.

If $R^4$ is different from hydrogen, $R^4$ is in particular selected from the group consisting of halogen, especially fluorine, a radical $OR^{42}$, where $R^{42}$ is as defined above, and a group $Z^4$—$Ar^4$, where $Z^4$ and $Ar^4$ are as defined above.

$R^4$ is in particular selected from the group consisting of hydrogen, halogen, especially fluorine and a radical $OR^{42}$, where $R^{42}$ is as defined above. $R^4$ may also be a group $Z^4$—$Ar^4$, where $Z^4$ and $Ar^4$ are as defined above.

If $R^4$ is a radical $OR^{42}$ then $R^{42}$ is in particular $C_1$-$C_4$-alkyl, such as methyl, or $C_1$-$C_4$-haloalkyl, especially $C_1$-$C_2$-fluoroalkyl, such as difluoromethyl, trifluoromethyl, 2,2-difluoroethyl or 2,2,2-trifluoroethyl.

If $R^4$ is a moiety $Z^4$—$Ar^4$, $Z^4$ is preferably $CH_2$, 1,2-ethandiyl, 1,3-propandiyl, $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^4$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^4$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^4$ radical has at least one imino-nitrogen as ring member, which is located in the position adjacent to carbon atom bound to the group $Z^4$. Amongst these, particular preference is given to those, where $Ar^4$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^4$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

$R^4$ is in particular hydrogen, fluorine, chlorine, $C_1$-$C_4$-alkoxy or $C_1$-$C_4$-haloalkoxy and especially hydrogen, fluorine, chlorine, methoxy, fluoromethoxy, difluoromethoxy, trifluoromethoxy 2,2-difluoroethoxy or 2,2,2-trifluoroethoxy.

If $R^5$ is different from hydrogen, $R^5$ is in particular selected from the group consisting of halogen, especially fluorine, a radical $OR^{52}$, where $R^{52}$ is as defined above, $Y^1$—$NR^{57}R^{58}$, wherein $Y^1$, $R^{57}$ and $R^{58}$ are as defined herein, and a group $Z^5$—$Ar^5$, where $Z^5$ and $Ar^5$ are as defined herein.

$R^5$ is in particular selected from the group consisting of hydrogen, halogen, especially fluorine and a radical $OR^{52}$, where $R^{52}$ is as defined above. $R^5$ may also be a group $Z^5$—$Ar^5$, where $Z^5$ and $Ar^5$ are as defined above.

If $R^5$ is a radical $OR^{52}$ then $R^{52}$ is in particular $C_1$-$C_4$-alkyl, such as methyl, or $C_1$-$C_4$-haloalkyl, especially $C_1$-$C_2$-fluoroalkyl, such as difluoromethyl or trifluoromethyl.

If $R^5$ is a radical $Y^1$—$NR^{57}R^{58}$, $Y^1$ is in particular a single bond or $CH_2$. $R^{57}$ and $R^{58}$ are in particular, independently of each other $C_1$-$C_4$-alkyl or hydroxyl-$C_2$-$C_4$-alkyl., or $NR^{57}R^{58}$ forms a saturated or aromatic N-bound 5-, 6- or 7-membered heterocyclyl, which in addition to the nitrogen atom may have 1 or 2 further heteroatom moieties as ring members, which are selected from the group consisting of O, N, S, S(O), $S(O)_2$ or N—$R^x$, where heterocyclyl is unsubstituted or carries 1, 2, 3 or 4 $C_1$-$C_4$-alkyl groups and where $R^x$ is hydrogen or methyl. Examples of such cyclic moieties $NR^{57}R^{58}$ are morpholinyl, pyrrolidinyl, piperazinyl, N-methylpiperazinyl, 1H-imidazol-1-yl, 4-methyl-2-ethyl-1H-imidazol-1-yl or 4-methyl-2-isopropyl-1H-imidazol-1-yl, If $R^5$ is a moiety $Z^5$—$Ar^5$, $Z^5$ is preferably $CH_2$, 1,2-ethandiyl, 1,3-propandiyl, $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^5$ is in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^5$ is more particularly selected from the group consisting of C-bound, 9- or 10-membered, fused bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^5$ radical has at least one imino-nitrogen as ring member, which is located in the position adjacent to carbon atom bound to the group $Z^5$. Amongst these, particular preference is given to those, where $Ar^5$ is selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^5$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

In particular embodiments of the invention $R^4$ and $R^5$, together with the carbon atoms, to which they are attached, may also form a fused 5-, 6- or 7-membered saturated heterocyclic ring, where the fused heterocyclic ring has 1 or 2 oxygen atoms as ring members and where the fused heterocyclic ring is unsubstituted or may carry 1 or 2 radicals selected from methyl, methoxy and fluorine. In particular the radicals $R^4$ and $R^5$ together may form a moiety $OCH_2O$ or $OCF_2O$. In these particular embodiments, $R^3$ is preferably hydrogen.

$R^5$ is in particular hydrogen, fluorine, $C_1$-$C_4$-alkoxy or $C_1$-$C_4$-haloalkoxy and especially fluorine, chlorine, methoxy, fluoromethoxy, difluoromethoxy, trifluoromethoxy, 2,2-difluoroethoxy or 2,2,2-trifluoroethoxy.

Particularly preferred embodiments of the inventions relate to compounds of the formulae I, I-A, I-B, I-C and I-D, wherein $R^3$ is methoxy, difluoromethoxy, trifluoromethoxy, 2,2-difluoroethoxy or 2,2,2-trifluoroethoxy, $R^4$ is hydrogen and $R^5$ is fluorine, chlorine, methoxy, difluoromethoxy, trifluoromethoxy, 2,2-difluoroethoxy or 2,2,2-trifluoroethoxy.

Particularly preferred embodiments of the inventions also relate to compounds of the formulae I, I-A, I-B, I-C and I-D, wherein $R^3$ is hydrogen, $R^4$ is fluorine, chlorine, methoxy, difluoromethoxy, trifluoromethoxy, 2,2-difluoroethoxy or 2,2,2-trifluoroethoxy and $R^5$ is fluorine, chlorine, methoxy, difluoromethoxy, trifluoromethoxy, 2,2-difluoroethoxy or 2,2,2-trifluoroethoxy, provided that at least one of the radicals $R^4$ and $R^5$ is methoxy, difluoromethoxy, trifluoromethoxy, 2,2-difluoroethoxy or 2,2,2-trifluoroethoxy.

Particularly preferred embodiments of the inventions also relate to compounds of the formulae I, I-A, I-B, I-C and I-D, wherein $R^5$ is hydrogen, $R^4$ is fluorine, chlorine methoxy, difluoromethoxy, trifluoromethoxy, 2,2-difluoroethoxy or 2,2,2-trifluoroethoxy and $R^3$ is fluorine, chlorine methoxy, difluoromethoxy, trifluoromethoxy, 2,2-difluoroethoxy or 2,2,2-trifluoroethoxy, provided that at least one of the radicals $R^3$ and $R^5$ is methoxy, difluoromethoxy, trifluoromethoxy, 2,2-difluoroethoxy or 2,2,2-trifluoroethoxy.

Particularly preferred embodiments of the inventions also relate to compounds of the formulae I, I-A, I-B, I-C and I-D, wherein $R^3$ is hydrogen, $R^4$ is hydrogen and $R^5$ is halogen, fluorine, chlorine, methoxy, difluoromethoxy, trifluoromethoxy, 2,2-difluoroethoxy or 2,2,2-trifluoroethoxy.

Particularly preferred embodiments of the inventions also relate to compounds of the formulae I, I-A, I-B, I-C and I-D, wherein $R^3$ is hydrogen, $R^4$ is hydrogen and $R^5$ is $NR^{57}R^{58}$ which forms a saturated N-bound 5-, 6- or 7-membered heterocyclyl, which in addition to the nitrogen atom may have 1 or 2 further heteroatom moieties as ring members, which are selected from the group consisting of O, N, S, S(O), S(O)$_2$ or N—$R^x$, where heterocyclyl is unsubstituted or carries 1, 2, 3 or 4 methyl groups and where $R^x$ is hydrogen or methyl. Examples of such cyclic moieties $NR^{57}R^{58}$ are 4-morpholinyl, 1-pyrrolidinyl, 1-piperazinyl and N-methyl-1-piperazinyl.

Particularly preferred embodiments of the inventions also relate to compounds of the formulae I, I-A, I-B, I-C and I-D, wherein $R^3$ is hydrogen, $R^4$ is hydrogen and $R^5$ is a moiety $Z^5$—$Ar^5$, wherein $Z^5$ is as defined above and in particular selected from the group consisting of $CH_2O$, $OCH_2$, $CH_2CH_2O$ or $OCH_2CH_2$, wherein 1, 2, 3 or 4 hydrogen atoms may be replaced by a fluorine atom. In these embodiments, $Ar^y$ is as defined above and in particular C-bound 6-membered monocyclic hetaryl, which has 1 or 2 nitrogen atoms as ring members, or C-bound, 9- or 10-membered, fused bicyclic hetaryl, which has 1 or 2 nitrogen atoms as ring members and optionally a further heteroatom selected from O, S and N as ring member, such as 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl or 1,2,4-triazolo[1,5-a]pyridine-2-yl, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Particularly preferred embodiments of the inventions also relate to compounds of the formulae I, I-A, I-B, I-C and I-D, wherein $R^3$ is hydrogen and $R^4$ and $R^5$, together with the carbon atoms, to which they are attached, form a fused 5-, 6- or 7-membered saturated heterocyclic ring, where the fused heterocyclic ring has 1 or 2 oxygen atoms as ring members and where the fused heterocyclic ring is unsubstituted or may carry 1 or 2 radicals selected from methyl, methoxy and fluorine. In particular the radicals $R^4$ and $R^5$ together may form a moiety $OCH_2O$ or $OCF_2O$.

In the aforementioned particularly preferred embodiments X is preferably CH or C—$OCH_3$.

Apart from that, the variables $Ar^2$, $Ar^3$, $Ar^7$, $R^{Ar}$, $Z^2$, $Z^3$, $Z^7$, $Y^1$, $Y^2$, $Y^3$, $Y^4$, $Y^5$, $Y^6$, $R^x$, $R^y$, $R^{yy}$, $R^{y1}$, $R^{y2}$, $R^{y3}$, $R^{y4}$, $R^{y5}$, $R^{y6}$, $R^{y7}$, $R^{y8}$, $R^{y9}$, $R^{y0}$, $R^z$, $R^{Ar1}$, $R^{Ar2}$, $R^{Ar3}$, $R^{Ar4}$, $R^{Ar5}$, $R^{Ar6}$, $R^{Ar7}$, $R^{Ar8}$, $R^{Ar9}$, $R^{Ar0}$, $R^{12}$, $R^{13}$, $R^{14}$, $R^{15}$, $R^{15a}$, $R^{16}$, $R^{17}$, $R^{18}$, $R^{19}$, $R^{22}$, $R^{23}$, $R^{24}$, $R^{25}$, $R^{26}$, $R^{27}$, $R^{28}$, $R^{31}$, $R^{33}$, $R^{34}$, $R^{35}$, $R^{35a}$, $R^{36}$, $R^{37}$, $R^{38}$, $R^{39}$, $R^{41}$, $R^{43}$, $R^{44}$, $R^{45}$, $R^{45a}$, $R^{46}$, $R^{47}$, $R^{48}$, $R^{49}$, $R^{51}$, $R^{53}$, $R^{54}$, $R^{55}$, $R^{55a}$, $R^{56}$, $R^{57}$, $R^{58}$, $R^{59}$, $R^{61}$, $R^{62}$, $R^{63}$, $R^{64}$, $R^{65}$, $R^{65a}$, $R^{66}$, $R^{67}$, $R^{68}$, $R^{69}$, $R^{71}$, $R^{72}$, $R^{73}$, $R^{74}$, $R^{75}$ and $R^{76}$ particularly have, irrespectively of their occurrence and with regard to the formulae I, I-A, I-B, I-C and I-D and with regard to each of the above mentioned embodiments, groups of embodiments and particularly preferred embodiments one of the following meanings:

$Ar^2$, $Ar^3$ and $Ar^7$, independently of each other, are in particular selected from the group consisting of C-bound 6-membered monocyclic hetaryl, which has 1 or 2 nitrogen atoms as ring members, and C-bound, 9- or 10-membered, fused bicyclic hetaryl, which has 1 or 2 nitrogen atoms as ring members and optionally a further heteroatom selected from O, S and N as ring member, where monocyclic hetaryl and bicyclic hetaryl may be unsubstituted or may carry 1, 2 or 3 substituents $R^{Ar}$, in particular 0, 1 or 2 substituents $R^{Ar}$. In this regard, $R^{Ar}$ is preferably selected from halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, and fluorinated $C_3$-$C_6$-cycloalkyl. In this regard, $R^{Ar}$ is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

$Ar^2$, $Ar^3$ and $Ar^7$, independently of each other, are more particularly selected from the group consisting of fused, 9- or 10-membered bicyclic hetaryl, which has 1 or 2 nitrogen atoms as ring members and optionally a further heteroatom selected from O, S and N as ring member and which may be unsubstituted or may carry 1, 2 or 3 substituents $R^{Ar}$, in particular 0, 1 or 2 substituents $R^{Ar}$ as defined above. Amongst these, particular preference is given to those compounds, where the $Ar^4$ radical has at least one imino-nitrogen as ring member, which is located in the position adjacent to carbon atom bound to the groups $Z^2$, $Z^3$ or $Z^7$, respectively. Amongst these, particular preference is given to those, where $Ar^2$, $Ar^3$ and $Ar^7$, independently of each other are selected from the group consisting of C-bound, 9- or 10-membered, fused bicyclic hetaryl, which has 1 or 2 nitrogen atoms as ring members and optionally a further heteroatom selected from O, S and N as ring member, where bicyclic hetaryl may be unsubstituted or may carry 1, 2 or 3 substituents $R^{Ar}$, in particular 0, 1 or 2 substituents $R^{Ar}$.

Particular examples of $Ar^2$, $Ar^3$ and $Ar^7$ are selected from the group consisting of 2-benzofuryl, 2-pyridyl, 2-pyrimidinyl, 4-pyrimidinyl, 2-pyrazinyl, 3-pyridazinyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^{Ar}$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, and fluorinated cyclopropyl.

$Z^2$ is in particular a single bond, $CH_2$, $CH_2CH_2$, $CH_2O$ or $CH_2CH_2O$, wherein 1, 2, 3 or 4 hydrogen atoms may be replaced by a fluorine atom.

$Z^3$ is in particular a O, $OCH_2$ or $OCH_2CH_2$, wherein 1, 2, 3 or 4 hydrogen atoms may be replaced by a fluorine atom.

$Z^7$ is in particular a single bond, $CH_2$, $CH_2CH_2$, $CH_2O$, $CH_2CH_2O$, $OCH_2$ or $OCH_2CH_2$, wherein 1, 2, 3 or 4 hydrogen atoms may be replaced by a fluorine atom.

$Y^1$ is in particular a single bond, $CH_2$, $CH_2CH_2$, $OCH_2$, $OCH_2CH_2$, $C(=O)$, $OC(=O)$, $CH_2C(=O)$.

$Y^2$ is in particular a single bond, O, $CH_2O$, $CH_2CH_2O$, $C(=O)$, $C(=O)O$, $CH_2C(=O)$, $CH_2C(=O)O$ or $SO_2$.

$Y^3$ is in particular a single bond, $CH_2$, $CH_2CH_2$ or $C(=O)$.

$Y^5$, $Y^6$, independently of each other, are in particular a single bond, $CH_2$ or $CH_2CH_2$.

$R^{31}$, $R^{41}$, $R^{51}$, $R^{61}$, $R^{61}$, $R^{71}$, $R^{y1}$, $R^{Ar1}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl, more especially methyl, difluoromethyl or trifluoromethyl.

$R^{12}$, $R^{22}$, $R^{62}$, $R^{72}$, $R^{y2}$, $R^{Ar2}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl.

$R^{13}$, $R^{33}$, $R^{43}$, $R^{53}$, $R^{63}$, $R^{73}$, $R^{y3}$, $R^{Ar3}$, independently of each other, are in particular $C_1$-$C_4$-alkyl or $C_1$-$C_4$-haloalkyl, especially methyl, ethyl, difluoromethyl or trifluoromethyl.

$R^{14}$, $R^{23}$, $R^{34}$, $R^{44}$, $R^{54}$, $R^{64}$, $R^{74}$, $R^{y4}$, $R^{Ar4}$, independently of each other, are in particular $C_1$-$C_4$-alkyl, $C_1$-$C_4$-haloalkyl, $C_3$-$C_6$-cycloalkyl or $C_3$-$C_6$-cycloalkylmethyl, especially methyl, ethyl, difluoromethyl, trifluoromethyl, cyclopropyl, cyclobutyl or cyclopropylmethyl;

$R^{15}$, $R^{24}$, $R^{35}$, $R^{45}$, $R^{55}$, $R^{65}$, $R^{75}$, $R^{y5}$, $R^{Ar5}$, independently of each other, are in particular $C_1$-$C_4$-alkyl, $C_3$-$C_6$-cycloalkyl or $C_3$-$C_6$-cycloalkylmethyl, especially methyl, ethyl, cyclopropyl, cyclobutyl or cyclopropylmethyl.

$R^{16}$, $R^{36}$, $R^{46}$, $R^{56}$, $R^{66}$, $R^{76}$, $R^{y6}$, $R^{Ar6}$, independently of each other, are in particular $C_1$-$C_4$-alkyl, $C_1$-$C_4$-haloalkyl, $C_3$-$C_6$-cycloalkyl or $C_3$-$C_6$-cycloalkylmethyl, especially methyl, ethyl, difluoromethyl, trifluoromethyl, cyclopropyl, cyclobutyl or cyclopropylmethyl.

$R^{17}$, $R^{25}$, $R^{37}$, $R^{47}$, $R^{57}$, $R^{67}$, $R^{y7}$, $R^{Ar7}$, independently of each other, are in particular hydrogen, $C_1$-$C_4$-alkyl or $C_3$-$C_4$-alkenyl, especially hydrogen, methyl, ethyl, propyl, isopropyl or 2-propenyl.

$R^{18}$, $R^{26}$, $R^{48}$, $R^{58}$, $R^{68}$, $R^{y8}$, $R^{Ar8}$, independently of each other, are in particular hydrogen, $C_1$-$C_4$-alkyl or $C_3$-$C_4$-alkenyl, especially hydrogen, methyl, ethyl, propyl, isopropyl or 2-propenyl.

$R^{17}$ and $R^{18}$, $R^{25}$ and $R^{26}$, $R^{37}$ and $R^{38}$, $R^{47}$ and $R^{48}$, $R^{57}$ and $R^{58}$, $R^{67}$ and $R^{68}$, $R^{y7}$ and $R^{y8}$, or $R^{Ar7}$ and $R^{Ar8}$, respectively, together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl and fluorine.

$R^{19}$, $R^{27}$, $R^{39}$, $R^{49}$, $R^{59}$, $R^{69}$, $R^{y9}$, $R^{Ar9}$, $R^z$, independently of each other, are in particular hydrogen, $C_1$-$C_4$-alkyl or $C_3$-$C_4$-alkenyl, especially hydrogen, methyl, ethyl, propyl, isopropyl or 2-propenyl;

$R^{15a}$, $R^{25a}$, $R^{35a}$, $R^{45a}$, $R^{55a}$, $R^{65a}$, $R^{y0}$, $R^{Ar0}$, independently of each other, are in particular trimethylsilyl, $C_1$-$C_4$-alkyl, $C_1$-$C_4$-haloalkyl, $C_3$-$C_6$-cycloalkyl, $C_3$-$C_6$-cycloalkylmethyl or $C_3$-$C_4$-alkenyl, especially methyl, ethyl, difluoromethyl, trifluoromethyl, cyclopropyl, cyclobutyl or cyclopropylmethyl, more especially methyl, difluoromethyl or trifluoromethyl.

$R^y$ is in particular selected from the group consisting of OH, CN, $C_1$-$C_4$-alkoxy, especially methoxy, and $C_1$-$C_4$-hydroxyalkoxy, especially 2-hydroxyethoxy.

$R^x$ is in particular selected from the group consisting of hydrogen and $C_1$-$C_4$-alkyl, especially methyl.

$R^{yy}$ is in particular selected from the group consisting of halogen, especially fluorine, $C_1$-$C_4$-alkyl, especially methyl, $C_1$-$C_4$-alkoxy, especially methoxy, $C_1$-$C_2$-fluoroalkyl such as difluoromethyl or trifluoromethyl, and $C_1$-$C_2$-fluoroalkoxy such as difluoromethoxy or trifluoromethoxy.

Particular embodiments of the invention relates to the compounds of formula I, to the N-oxides, the prodrugs, the hydrates and the tautomers thereof and to the pharmaceutically suitable salts thereof, where the compounds of the formula I are selected from the group consisting of:

6,8-difluoro-3-methyl-1-(2-methylpyridine-3-yl)-3H-2,3,4,5-tetraazacyclopenta[a]naphthalene, 6,8-difluoro-3-methyl-1-(2-chlorophenyl)-3H-2,3,4,5-tetraazacyclopenta[a]naphthalene, 6,8-dimethoxy-3-methyl-1-(2-methylpyridine-3-yl)-3H-2,3, 4,5-tetraazacyclopenta[a]naphthalene,
1-hydroxy-6,8-dimethoxy-3-methyl-3H-2,3,4,5-tetraazacyclopenta[a]naphthalene,
6,8-dimethoxy-3-methyl-1-(2-chlorophenyl)-3H-2,3,4,5-tetraazacyclopenta[a]naphthalene,
8-fluoro-6-methoxy-3-methyl-1-(3-methylpyridine-4-yl)-3H-2,3,4,5-tetraazacyclopenta[a]naphthalene,
8-fluoro-6-methoxy-3-methyl-1-(2-methylpyridine-3-yl)-3H-2,3,4,5-tetraazacyclopenta[a]naphthalene,
8-fluoro-6-methoxy-3-methyl-1-(2-chlorophenyl)-3H-2,3,4, 5-tetraazacyclopenta[a]naphthalene,
8-fluoro-6-methoxy-3-methyl-3H-2,3,4,5-tetraazacyclopenta[a]naphthalene,
6-fluoro-8-methoxy-3-methyl-1-(3-methylpyridine-4-yl)-3H-2,3,4,5-tetraazacyclopenta[a]naphthalene,
6-fluoro-8-methoxy-3-methyl-1-(2-chlorophenyl)-3H-2,3,4, 5-tetraazacyclopenta[a]naphthalene,
1-hydroxy-6-fluoro-8-methoxy-3-methyl-3H-2,3,4,5-tetraazacyclopenta[a]naphthalene,
6-fluoro-8-methoxy-3-methyl-1-morpholin-4-yl-3H-2,3,4, 5-tetraazacyclopenta[a]naphthalene,
7,8-dimethoxy-1,3-dimethyl-3H-2,3,4,5-tetraazacyclopenta [a]naphthalene,
7,8-dimethoxy-3-methyl-1-(3,5-dimethoxyphenyl)-3H-2,3, 4,5-tetraazacyclopenta[a]naphthalene,
7,8-dimethoxy-3-methyl-1-(5-methylpyridine-3-yl)-3H-2,3, 4,5-tetraazacyclopenta[a]naphthalene,
1-hydroxy-7,8-dimethoxy-3-methyl-3H-2,3,4,5-tetraazacyclopenta[a]naphthalene,
1-cyclopropyl-6-fluoro-8-methoxy-3-methyl-3H-2,3,4,5-tetraazacyclopenta[a]naphthalene,
1,6,8-trimethoxy-3-methyl-pyrazolo[3,4-c]cinnoline,
1-isobutyl-6,8-dimethoxy-3-methyl-pyrazolo[3,4-c]cinnoline,
1-cyclopropyl-6,8-dimethoxy-3-methyl-pyrazolo[3,4-c]cinnoline,
7,8-dimethoxy-1-methyl-3H-2,3,4,5-tetraaza-cyclopenta[a]naphthalene,
8-fluoro-6-methoxy-3-methyl-3H-2,3,4,5-tetraaza-cyclopenta[a]naphthalene,
5-(6,8-dimethoxy-3-methyl-pyrazolo[3,4-c]cinnolin-1-yl)-2,4-dimethyl-thiazole,
3-(6,8-dimethoxy-3-methyl-pyrazolo[3,4-c]cinnolin-1-yl) benzamide
and the N-oxides, the tautomers, the hydrates, the prodrugs and the pharmaceutically acceptable salts thereof.

The compounds of the invention of the general formulae I, I-A, I-B, I-C and I-D and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2nd edition, Weinheim, 1999 and the literature cited therein. The compounds of the invention of the general formula I are advantageously prepared by the methods described below and/or in the experimental section.

Compounds of the formula I, wherein $R^1$ is selected from a C-bound radicals, such as $Z^1$—$Ar^1$ with $Z^1$ being a single bond or $C_1$-$C_4$-alkylene or $R^{11}$, can be prepared e.g. by reacting a compound of the formula I, wherein $R^1$ is a suitable leaving group LG, such as chlorine, bromine or iodine, triflate or nonaflate, with a compound M-$R^1$, hereinafter also termed compound II, as depicted in scheme 1.

Scheme 1:

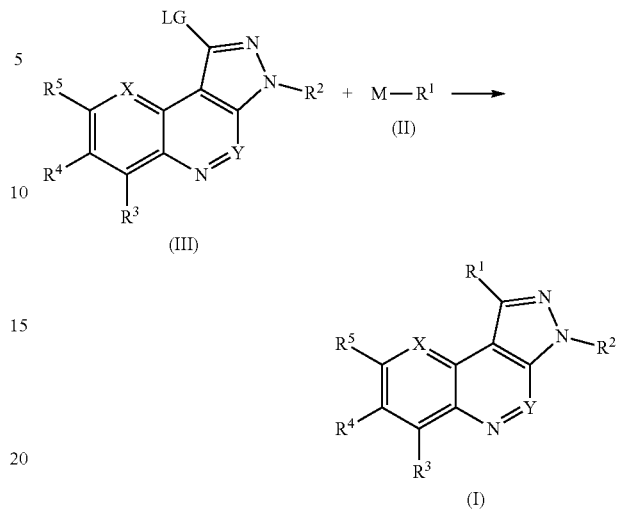

Compound of formula III corresponds to compound of formula I, where R1 is a leafing group LG. Suitable leafing groups LG in formula III include, but are not limited to halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate. In formula I, M relates to a metal or metal bound organometal group, such as Li, MgHal, ZnHal, with Hal being Cl, Br or I, a group Sn($R^{Sn}$)$_3$ wherein $R^{Sn}$ is $C_1$-$C_6$-alkyl or $C_3$-$C_6$-cycloalkyl or phenyl. M may also be B(O$R^{B1}$)(O$R^{B2}$) radical, where $R^{B1}$ and $R^{B2}$ are, independently of each other, hydrogen or $C_1$-$C_4$-alkyl or $R^{B1}$ and $R^{B2}$ together form a $C_2$-$C_6$-alkandiyl moiety, e.g. ethan-1,2-diyl, propan-1,3-diyl or 1,1,2,2-tetramethylethan-1,2-diyl.

The reaction of the compound II with the compound III can be performed by analogy to known coupling reactions in the presence of suitable transition metal catalysts, in particular palladium catalysts. Typical reactions conditions are those of Stille coupling and related reactions (see e.g. Stille et al. Angew. Chem. Int. Ed. Engl. 1986, 25,508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253, T. Zhang et al. Tetrahedron Lett., 52 (2011), 311-313, S. Bourrain et al., Synlett. 5 (2004), 795-798).

It is also possible to convert the compound of the formula III, wherein $R^1$ is halogen into the corresponding organometal compound, where $R^1$ is a group M as defined above.

Compounds of the formula I, where $R^1$ is a N-bound radical can be obtained by a coupling reaction between the compound II and the corresponding amine in the presence of a palladium catalyst in terms of a Buchwald-Hartwig reaction. Suitable palladium catalyst are for example tris-(dibenzylideneacetone)dipalladium(0) (Pd$_2$(dba)$_3$), [1,1-bis(diphenylphosphino)ferrocene]dichloropalladium(II) (PdCl$_2$(dppf)) or palladium acetate (Pd(OAc)$_2$). The reaction is usually carried out in the presence of a tri(substituted) phosphine, e.g. a triarylphosphine such as triphenylphosphine, tritolylphosphine or 2,2'-bis(diphenylphosphino)-1, 1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

Compounds of the formula I, where $R^1$ is a O-bound radical or an S-bound radical can be obtained by a coupling reaction between the compound II and the corresponding alcohol or mercaptan in the presence of a strong base.

Compounds of the formula I, where $R^1$ is a $C(O)OR^{14}$ radical can be prepared by esterification of the corresponding acid, where R1 is C(O)OH.

Compounds of the formula I, where $R^1$ is a $OC(O)R^{16}$ radical can be prepared from the corresponding OH compound, where $R^1$ is OH, by an esterification.

Compounds of the formula I, where $R^1$ halogen, in particular chlorine, bromine or iodine, can be prepared from the corresponding OH compound, where $R^1$ is OH.

Compounds of the formula I, where $R^1$ halogen, in particular chlorine or bromine, can also be prepared by selective halogenation of the corresponding unsubstituted compound, where $R^1$ is hydrogen.

The compounds of formula I, where Y is N, may also be prepared by intramolecular cyclization of a diazonium compound, which is prepared from the corresponding 5-amino-4-arylpyrazole compound of formula IV as depicted in scheme 2:

Scheme 2:

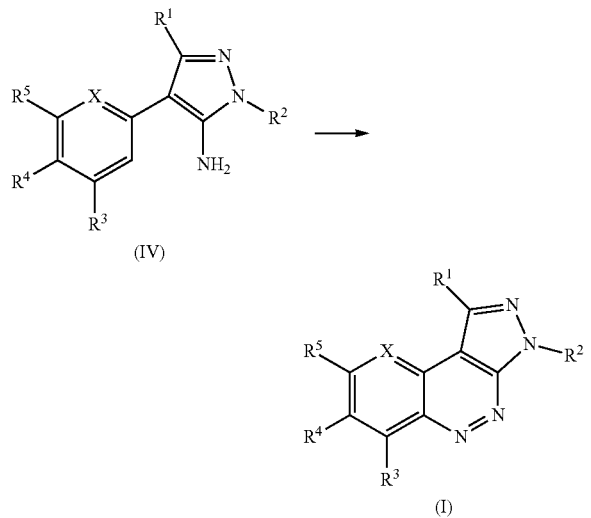

The intramolecular cyclization of the compound IV, via its diazonium compound, to the compound IV can be performed by analogy to known intramolecular cyclization reactions. Typical reactions conditions are those described by C. L. Bogza et al. in Chemistry of Heterocyclic Compounds, Vol. 40, (2004), 1506.

The compounds of formula I, where Y is N and $R^1$ is OH, may also be prepared by two-step intramolecular cyclization of 5-amino-4-(o-nitroaryl)pyrazole compound of formula V as depicted in scheme 3:

Scheme 3:

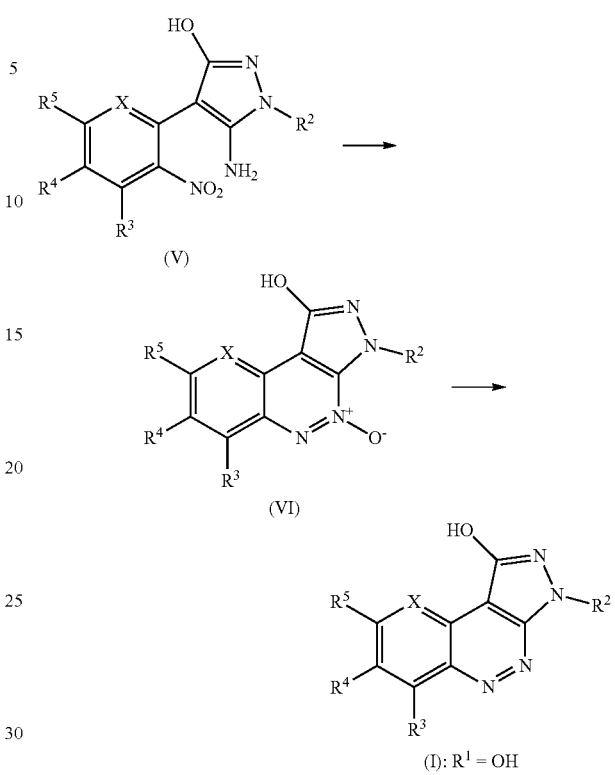

The intramolecular cyclization of the compound V, via the N-oxide VI to the compound I can be performed by analogy to the Method described by M. Scobie et al. in J. Chem. Soc., Chem. Commun, 1993, 1756.

Compounds, wherein Y is $C-R^7$ can be prepared by analogy to the methods described in US2009075980, J. Org. Chem. 65 (2000) pp. 9001-9006, J. Org. Chem. 66 (2001) pp. 4214-4219, J. Org. Chem. 67 (2002) pp. 585-586 and Tetrahedron 58, 2002, 7635.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from $-10°$ C. to $100°$ C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance use disorders in a mammalian;
a method for treating, controlling or ameliorating substance (drug) abuse;
a method for treating or ameliorating the symptoms associated with diet-induced obesity in a mammalian;
a method for treating, controlling, ameliorating or reducing the risk of cognitive disturbances associated with Alzheimer's disease in a mammalian;
a method for treating, controlling, ameliorating or reducing the risk of behavioral symptoms in Alzheimer's disease;
a method for treating, controlling, ameliorating or reducing the risk of anxiety in a mammalian;
a method for treating, controlling, ameliorating or reducing the risk of Huntington's disease in a mammalian;
which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

EXAMPLES

Abbreviations:
AcOH acetic acid
DCM dichloromethane
DMF dimethylformamide
DMSO dimethylsulfoxide
EA ethyl acetate
EtOH ethanol
hr hour
MeOH methanol
PE petrolether
pre-TLC preperative thin layer chromatography
r.t. room temperature
RT retention time
TEA triethylamine
TFA trifluoroacetic acid
Tf$_2$O trifluoromethanesulfonic anhydride
THF tetrahydrofuran The compounds were either characterized via proton-NMR in d$_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

I. Preparation Examples

Example 1

6,8-Difluoro-3-methyl-3H-pyrazolo[3,4-c]cinnolin-1-ol 1.1 ethyl 2-cyano-2-(3,5-difluorophenyl)acetate 0.75 g (32.6 mmol) of sodium in small pieces were added gradually to a solution of 5 g (32.6 mmol) of (3,5-difluorophenyl)-acetonitrile in 50 mL of diethyl carbonate in such a manner that the temperature remained at approximately 100° C. Thereafter, the reaction mixture was heated to reflux for 1 hr. After evaporation under reduced pressure, the mixture was treated with cooled water. The solution was acidified with 20 mL of glacial acetic acid and extracted with EA. The combined organic extracts were dried and evaporated. The residue was purified by silica gel (EA:PE/1:10) to give 6.5 g of the title compound as light brown oil (yield: 88%).

LC-MS: m/z 226 (M+H); RT=1.75 min/2.5 min 1.2 5-amino-4-(3,5-difluorophenyl)-1-methyl-1H-pyrazol-3-ol In a 500 mL reflux condenser, a mixture of 5.0 g (22.2 mmol) of the compound from example 1.1 and 37 g (222 mmol) of methylhydrazine sulfate in 100 mL of ethanol and 50 mL of H$_2$O was stirred at 90° C. for overnight. The reaction mixture was filtered, the filtrate was concentrated to afford the solid which was washed with ethanol and DCM to give 1.4 g of the title compound (yield: 25%).

LC-MS: m/z 226 (M+H); RT=1.34 min/2.5 min
$^1$H NMR (400 MHz, d$_6$-DMSO): δ=7.42 (d, J=8.4 Hz, 1H), 7.27 (d, J=8.4 Hz, 2H), 6.81~6.74 (m, 1H), 6.54~6.55 (m, 1H), 6.10 (s, 1 H), 3.24 (s, 3 H).

1.3 6,8-difluoro-3-methyl-3H-pyrazolo[3,4-c]cinnolin-1-ol

A solution of 0.6 g (2.66 mmol) of the compound from example 1.2 in 15 mL of water and 7.5 mL of conc. HCl was treated with 0.92 g (13.3 mmol) of sodium nitrite maintaining the temperature of the reaction mixture at 0° C. The mixture was stirred additionally for 12 hr at RT and evaporated to dryness. The residue was purified by silica gel (PE:EA/5:1) to give 0.3 g of the title compound as yellow solid (yield: 54%).

LC-MS: m/z 237 (M+H); RT=1.52 min/2.5 min $^1$H NMR (400 MHz, d$_6$-DMSO): δ=11.96 (d, 1H), 7.73~7.75 (m, 2 H), 4.23 (s, 1 H).

Example 2

1-(2-Chlorophenyl)-6,8-difluoro-3-methyl-3H-pyrazolo[3,4-c]cinnoline 2.1 7,8-dimethoxy-3-methyl-3H-pyrazolo[3,4-c]cinnolin-1-yltrifluoromethanesulfonate Under nitrogen atmosphere and in a 50 mL round-bottomed flask, the compound from example 1 (0.30 g, 1.27 mmol) was added to 30 mL of THF to give a yellow suspension, and then TEA (0.71 mL, 5.08 mmol) was added. The suspension was cooled to −78° C. in a dry ice/acetone bath. Trifluoromethanesulfonic anhydride (0.43 mL, 2.54 mmol) was injected over 1 min to the suspension. After stirred at −78° C. for 45 min, the reaction mixture was allowed warming to room temperature. The suspension was diluted with 50 mL of EA, then washed with brine (1×50 mL). The organic layer was dried over Na$_2$SO$_4$, concentrated to give 300 mg of the title compound (yield: 64%) as brown solid. It was used directly to next step without further purification.

LC-MS: m/z 369 (M+H); RT=1.84 min/2.5 min 2.2 1-(2-chlorophenyl)-6,8-difluoro-3-methyl-3H-pyrazolo[3,4-c]cinnoline K$_2$CO$_3$ (18.8 mg, 0.136 mmol), 2-chlorophenylboronic acid (17.0 mg, 0.11 mmol) and Pd(Ph$_3$P)$_4$ (6.28 mg, 0.005 mmol) were each added sequentially to the microwave reaction vial. A solution of the compound from example 2.1 (20 mg, 0.054 mmol) in 2 mL of dioxane and 0.5 mL of H$_2$O was injected into the reaction vial. The reaction was heated in a Biotage microwave at 100° C. for 1 hr. The reaction mixture was filtered and concentrated to dryness to give a brown solid, which was purified by pre-HPLC to give 1.4 mg of the title compound (yield: 7.5%).

LC-MS: m/z 331 (M+H); RT=1.90 min/2.5 min $^1$H NMR (400 MHz, d$_6$-DMSO): δ=7.65~7.63 (m, 1H), 7.60~7.58 (m, 1 H), 7.56~7.52 (m, 1 H), 7.50~7.46 (m, 1 H), 7.25~7.20 (m, 1 H), 7.17~7.14 (m, 1 H), 4.61 (s, 3 H).

Example 3

6,8-Difluoro-3-methyl-1-(2-methylpyridin-3-yl)-3H-pyrazolo[3,4-c]cinnoline

K$_2$CO$_3$ (28.1 mg, 0.204 mmol), 2-methylpyridin-3-ylboronic acid (22.3 mg, 0.163 mmol) and Pd(Ph$_3$P)$_4$ (9.41 mg, 0.008 mmol) were each added sequentially to the microwave reaction vial. A solution of the compound from example 2.1 (30 mg, 0.08 mmol) in 3 mL of dioxane and 0.5 mL of H$_2$O was injected into the reaction vial. The reaction was heated in a Biotage microwave at 100° C. for 1 hr. The reaction mixture was filtered and concentrated to dryness to give a brown solid, which was purified by pre-HPLC to give 2.5 mg of the title compound (yield: 10%).

LC-MS: m/z 332 (M+H); RT=1.30 min/2.5 min $^1$H NMR (400 MHz, d$_6$-DMSO): δ=8.81 (s, 1H), 8.17 (s, 1 H), 7.93~7.87 (m, 1 H), 7.66 (d, J=4.8 Hz, 1 H), 7.15~7.13 (m, 1 H), 4.45 (s, 3 H), 2.45 (s, 3 H).

Example 4

8-Fluoro-6-methoxy-3-methyl-3H-pyrazolo[3,4-c]cinnolin-1-ol 4.1 Ethyl 2-cyano-2-(3-fluoro-5-methoxyphenyl)acetate 4.2 g (181 mmol) of sodium in small pieces were added gradually to a solution of 25 g (151 mmol) of (3-fluoro-5-methoxyphenyl)-acetonitrile in 200 mL of diethyl carbonate in such a manner that the temperature remained at approximately 100° C. Thereafter, the reaction mixture was heated to reflux for 1 hr. After evaporation under reduced pressure, the mixture was treated with cooled water. The solution was acidified with acetic acid and extracted with EA. The combined organic extracts were dried and evaporated. The residue was purified by silica gel (EA:PE/1:10) to give 23 g of the title compound as light brown oil (yield: 64%).

LC-MS: m/z 238 (M+H); RT=1.72 min/2.5 min 4.2 5-amino-4-(3-fluoro-5-methoxyphenyl)-1-methyl-1H-pyrazol-3-ol In a 1000 mL reflux condenser, 10 g (42 mmol) of the compound from example 4.1 and 50 g (347 mmol) of methylhydrazine sulfate in 300 mL of ethanol and 150 mL of H$_2$O were added to give a yellow solution. The resulting solution was stirred at 90° C. over night. The reaction mixture was evaporated under reduced pressure, extracted with EA to give 3.4 g of the title compound (yield: 23%).

LC-MS: m/z 238 (M+H); RT=1.22 min/2.5 min 4.3 8-fluoro-6-methoxy-3-methyl-3H-pyrazolo[3,4-c]cinnolin-1-ol A solution of 1 g (4.2 mmol) of the compound from example 4.2 in 20 mL of water and 30 mL of conc. HCl was treated with 0.32 g (4.6 mmol) of sodium nitrite maintaining the temperature of the reaction mixture at 0° C. The mixture was stirred additionally for 1 hr at RT and evaporated to dryness. The residue was purified by HPLC to give 0.16 g of the title compound as yellow solid (yield: 15%).

LC-MS: m/z 249 (M+H); RT=1.42 min/2.5 min $^1$H NMR (400 MHz, d$_6$-DMSO): δ=11.75 (s, 1H), 7.41 (dd, J=9.2, 2.8 Hz, 1H), 7.19 (dd, J=11.2, 2.4 Hz, 1H), 4.19 (s, 3 H), 4.12 (s, 3 H).

Example 5

1-(2-Chlorophenyl)-8-fluoro-6-methoxy-3-methyl-3H-pyrazolo[3,4-c]cinnoline 5.1 8-fluoro-6-methoxy-3-methyl-3H-pyrazolo[3,4-c]cinnolin-1-yltrifluoromethanesulfonate Under nitrogen atmosphere and in a 50 mL round-bottomed flask, the compound from Example 4 (0.18 g, 0.73 mmol) was added to 200 mL of THF to give a yellow suspension, and then TEA (0.3 g, 3 mmol) was added. The suspension was cooled to −78° C. in a dry ice/acetone bath. The Tf$_2$O (0.42 g, 1.5 mmol) was injected over 1 min to the suspension. After stirred at −78° C. for 45 min, it allowed warming itself to room temperature. LC-MS indicated partial conversion to the product with SM remaining The suspension was diluted with 300 mL of EA, then washed with brine (1×200 mL). The organic layer was dried over Na$_2$SO$_4$, concentrated to give 450 mg of the title compound (yield: 100%) as brown solid. It was used directly to next step without further purification.

LC-MS: m/z 381 (M+H); RT=1.91 min/2.5 min 5.2 1-(2-chlorophenyl)-8-fluoro-6-methoxy-3-methyl-3H-pyrazolo[3,4-c]cinnoline The K₂CO₃ (54 mg, 0.236 mmol), 2-chlorophenylboronic acid (40 mg, 0.26 mmol) and Pd(Ph₃P)₄ (30 mg, 0.025 mmol) were each added sequentially to the microwave reaction vial. A solution of the compound from example 5.1 (50 mg, 0.131 mmol) in 2 mL of dioxane and 0.5 mL of H₂O was injected into the reaction vial. The reaction was heated in a Biotage microwave at 100° C. for 1 hr. The reaction mixture was filtered and concentrated to give a brown solid, which was purified by HPLC to give 10 mg of the title compound (yield: 22%).

LC-MS: m/z 342 (M+H); RT=1.68 min/2.5 min

¹H NMR (400 MHz, d₆-DMSO): δ=7.90~7.77 (m, 1H), 7.70~7.65 (m, 2H), 7.62~7.60 (m, 1H), 7.30 (dd, J=11.6, 2.4 Hz, 1H), 6.67 (dd, J=11.6, 2.4 Hz, 1H), 4.50 (s, 3 H), 4.14 (s, 3 H).

Example 6

8-Fluoro-6-methoxy-3-methyl-1-(2-methylpyridin-3-yl)-3H-pyrazolo[3,4-c]cinnoline The K₂CO₃ (54 mg, 0.236 mmol), 2-methylpyridin-3-ylboronic acid (36 mg, 0.26 mmol) and Pd(Ph₃P)₄ (30 mg, 0.025 mmol) were each added sequentially to the microwave reaction vial. A solution of the compound from example 5.1 (50 mg, 0.131 mmol) in 2 mL of dioxane and 0.5 mL of H₂O was injected into the reaction vial. The reaction was heated in a Biotage microwave at 100° C. for 1 hr. The reaction mixture was filtered and concentrated to give a brown solid, which was purified by HPLC to give 8 mg of the title compound (yield: 19%).

LC-MS: m/z 324 (M+H); RT=1.53 min/2.5 min

¹H NMR (400 MHz, d₆-DMSO): δ=8.71~8.69 (m, 1H), 7.94~7.91 (m, 1H), 7.49~7.46 (m, 1H), 7.30 (dd, J=11.6, 2.4 Hz, 1H), 6.64 (dd, J=11.6, 2.4 Hz, 1H), 4.50 (s, 3 H), 4.14 (s, 3 H), 2.35 (s, 3 H).

Example 7

6,8-Dimethoxy-3-methyl-3H-pyrazolo[3,4-c]cinnolin-1-ol 7.1 Ethyl 2-cyano-2-(3,5-dimethoxyphenyl)acetate 1.24 g (54.2 mol) of sodium in small pieces were added gradually to a solution of 8 g (45.1 mol) of (3,5-dimethoxyphenyl)-acetonitrile in 200 mL of diethyl carbonate in such a manner that the temperature remained at approximately 110° C. Thereafter, the reaction mixture was heated to reflux for 1 hr. After evaporation under reduced pressure, the mixture was treated with cooled water and acidified with acetic acid. The solution was extracted with EA and the combined organic layer were dried and evaporated. The residue was purified by column on silica gel (EA:PE/1:5) to give 8.73 g of the title compound as light brown oil (yield: 78%).

LC-MS (Method A): m/z 250 (M+H); RT=1.54 min/2.5 min 7.2 5-amino-4-(3,5-dimethoxyphenyl)-1-methyl-1H-pyrazol-3-ol In a 500 mL reflux condenser, a mixture of 8.73 g (35.0 mmol) of the compound from example 7.1 and 50.5 g (35 mmol) of methylhydrazine sulfate in 150 mL of ethanol and 100 mL of water was stirred at 90° C. over night. The reaction mixture was filtered, the solid was washed with EtOH and DCM to give 0.9 g of the title compound (yield: 10.3%).

LC-MS: m/z 250 (M+H); RT=1.18 min/2.5 min 7.3 6,8-dimethoxy-3-methyl-3H-pyrazolo[3,4-c]cinnolin-1-ol A solution of 0.9 g (3.61 mmol) of the compound from example 7.2 in 50 mL of water and 10 mL of conc. HCl was treated with 0.747 g (10.83 mmol) of sodium nitrite maintaining the temperature of the reaction mixture at 0° C. The mixture was stirred additionally for 1 hr at RT and evaporated to dryness. The residue was purified by silica gel (DCM: MeOH/100:1) to give 0.45 g of the title compound as yellow solid (yield: 48%).

LC-MS: m/z 261 (M+H); RT=1.035 min/2.5 min

¹H NMR (400 MHz, d₆-DMSO): δ=11.6 (brs, 1H), 7.14 (d, J=2.0 Hz 1 H), 6.8 (d, J=2.4 Hz 1 H), 4.13 (s, 3 H), 4.05 (s, 3 H), 3.98 (s, 3 H).

Example 8

1-(2-Chlorophenyl)-6,8-dimethoxy-3-methyl-3H-pyrazolo[3,4-c]cinnoline 8.1 6,8-dimethoxy-3-methyl-3H-pyrazolo[3,4-c]cinnolin-1-yltrifluoromethanesulfonate In a 100 mL round-bottomed flask, the compound from example 7 (250 mg, 0.96 mmol) was added to 60 mL of THF to give a yellow suspension under nitrogen atmosphere, then TEA (0.536 mL, 3.84 mmol) was added. The suspension was cooled to −78° C. in a dry ice/acetone bath. The Tf₂O (0.325 mL, 1.92 mmol) was injected over 5 min to the suspension. After stirred at −78° C. for 45 min, it allowed warming to room temperature. The suspension was diluted with 100 mL of EA, then washed with brine (1×50 mL). The organic layer was dried over Na₂SO₄, concentrated to give 170 mg of the title compound (45.1% yield) as brown solid. It was used directly to next step without further purification.

LC-MS: m/z 393 (M+H); RT=1.73 min/2.5 min 8.2 1-(2-chlorophenyl)-6,8-dimethoxy-3-methyl-3H-pyrazolo[3,4-c]cinnoline The cesium carbonate (116 mg, 0.357 mmol), 2-chlorophenylboronic acid (55.8 mg, 0.357 mmol) and PdCl₂(dppf) (13 mg, 0.018 mmol) were each added sequentially to a microwave reaction vial. A solution of the compound from example 8.1 (70 mg, 0.178 mmol) in 5 mL of 1,4-dioxane and 1 mL of water was injected into the reaction vial. The reaction was heated in a Biotage microwave at 100° C. for 1 hr. The reaction mixture was filtered and concentrated to dryness to give a brown solid, purified by HPLC to give 7 mg of the title compound (yield: 11%).

LC-MS: m/z 355 (M+H); RT=1.62 min/2.5 min

¹H NMR (400 MHz, d₆-DMSO): δ=7.77~7.58 (m, 4H), 6.89 (d, J=2.0 Hz 1 H), 6.44 (d, J=2.4 Hz 1 H), 4.45 (s, 3 H), 4.06 (s, 3 H), 3.7 (s, 3 H).

Example 9

6,8-Dimethoxy-3-methyl-1-(2-methylpyridin-3-yl)-3H-pyrazolo[3,4-c]cinnoline

The title compound was prepared in analogy to the method described in example 8.

LC-MS: m/z 335 (M+H); RT=1.49 min/2.5 min

¹H NMR (400 MHz, d₆-DMSO): δ=8.68~8.66 (m, 1H), 7.94~7.92 (m, 1H), 7.48~7.45 (m, 1H), 6.89 (d, J=2.0 Hz 1 H), 6.39 (d, J=2.0 Hz 1 H), 4.45 (s, 3 H), 4.08 (s, 3 H), 3.70 (s, 3 H), 2.39 (s, 3 H).

Example 10

7,8-Dimethoxy-3-methyl-3H-pyrazolo[3,4-c]cinnolin-1-ol 10.1 Ethyl 2-cyano-2-(3,4-dimethoxyphenyl)acetate 25.7 g (1.1 mol) of sodium in small pieces were added gradually to a solution of 198 g (1.1 mol) of (3,4-dimethoxyphenyl)-acetonitrile in 500 mL of diethyl carbonate in such a manner that the temperature remained at approximately 110° C. Thereafter, the reaction mixture was heated to reflux for 1 hr. The solvent was evaporated under reduced pressure and treated with cooled water. The solution was acidified with 70 mL of glacial acetic acid and extracted with EA. The combined organic extracts were dried and evaporated. The residue was purified by silica gel (EA:PE/1:5) to give 222 g of the title compound as light brown oil (yield: 80%).

LC-MS: m/z 250 (M+H); RT=1.04 min/1.7 min 10.2 5-amino-4-(3,4-dimethoxyphenyl)-1-methyl-1H-pyrazol-3-ol 30 g (120 mmol) of the compound from example 10.1 and 23 g (481 mmol) of methylhydrazine were added to 250 mL of EtOH to give a yellow solution. The resulting solution was stirred at 90° C. overnight. The reaction mixture was filtered, the solid was washed with EtOH to give 22.5 g of the title compound (yield: 75%).

LC-MS: m/z 250 (M+H); RT=1.28 min/3 min $^1$H NMR (400 MHz, $d_6$-DMSO): δ=9.44 (brs, 1H), 7.11 (d, J=2 Hz, 1H), 6.99~6.96 (m, 1H), 6.89~6.87 (m, 1H), 5.65 (s, 2H), 3.75 (s, 3 H), 3.72 (s, 3 H), 3.21 (s, 3 H).

10.3 7,8-dimethoxy-3-methyl-3H-pyrazolo[3,4-c]cinnolin-1-ol

A solution of 2.5 g (10 mmol) of the compound from example 10.2 in 20 mL of water and 3 mL of conc. HCl was treated with 0.69 g (10 mmol) of sodium nitrite maintaining the temperature of the reaction mixture at 0° C. The mixture was stirred for additional 1 hr at r.t. and then evaporated to dryness. The residue was purified by silica gel (DCM:MeOH/100:1) to give 1.18 g of the title compound as yellow solid (yield: 45%).

LC-MS: m/z 261 (M+H); RT=0.88 min/1.7 min $^1$H NMR (400 MHz, $d_6$-DMSO): δ=11.54 (brs, 1H), 7.95 (s, 1 H), 7.56 (s, 1 H), 4.13 (s, 3 H), 4.03 (s, 3 H), 4.00 (s, 3 H).

Example 11

7,8-Dimethoxy-3-methyl-1-(5-methylpyridin-3-yl)-3H-pyrazolo[3,4-c]cinnoline 11.1 7,8-dimethoxy-3-methyl-3H-pyrazolo[3,4-c]cinnolin-1-yltrifluoromethanesulfonate In a 50 mL round-bottomed flask, compound from example 10 (100 mg, 0.384 mmol) was added to 20 mL of THF to give a yellow suspension under nitrogen atmosphere, then TEA (0.214 mL, 1.537 mmol) was added. The suspension was cooled to −78° C. in a dry ice/acetone bath. The Tf$_2$O (0.130 mL, 0.768 mmol) was injected over 1 min to the suspension. After stirred at −78° C. for 45 min, it allowed warming to room temperature. The suspension was diluted with 50 mL of EA, then washed with sat. NaCl (1×50 mL). The organic layer was dried over Na$_2$SO$_4$, concentrated to give 90 mg of the title compound (59.7% yield) as brown solid. It was used directly to next step without further purification.

LC-MS: m/z 393 (M+H); RT=1.73 min/2.5 min 11.2 7,8-dimethoxy-3-methyl-1-(5-methylpyridin-3-yl)-3H-pyrazolo[3,4-c]cinnoline NaHCO$_3$ (193 mg, 2.294 mmol), 5-methylpyridin-3-yl-boronic acid (47.1 mg, 0.344 mmol) and Pd(Ph$_3$P)$_4$ (26.5 mg, 0.023 mmol) were added sequentially to a microwave reaction vial. Compound from example 11.1 (90 mg, 0.229 mmol) dissolved in 4 mL of toluene and 1 mL of EtOH and the resulting solution was injected into the reaction vial. The reaction was heated in a Biotage microwave at 100° C. for 1 hr. The reaction mixture was filtered and concentrated to dryness to give a brown solid which was purified by HPLC to give 15 mg of the title compound (yield: 20%).

LC-MS: m/z 336 (M+H); RT=1.44 min/2.5 min $^1$H NMR (400 MHz, $d_6$-DMSO): δ=8.87 (s, 1H), 8.61 (s, 1 H), 8.18 (s, 1 H), 8.09 (s, 1 H), 7.46 (s, 1 H), 4.46 (s, 3 H), 4.04 (s, 3 H), 3.86 (s, 3 H), 2.46 (s, 3 H).

The compounds of examples 12-26 were prepared following the same way shown above.

Example 12

6-Fluoro-8-methoxy-3-methyl-1-(3-methylpyridine-4-yl)-3H-2,3,4,5-tetraazacyclopenta[a]naphthalene LC-MS (: m/z 324 (M+H); RT=1.48 min/2.5 min $^1$H NMR (400 MHz, CDCl$_3$): δ=8.71 (brs, 2H), 7.49 (brs, 1H), 7.07 (dd, J=11.6, 2.4 1H), 6.77 (s, 1 H), 4.58 (s, 3 H), 3.74 (s, 3 H), 2.33 (s, 3 H).

Example 13

8-Fluoro-6-methoxy-3-methyl-1-(3-methylpyridine-4-yl)-3H-2,3,4,5-tetraazacyclopenta[a]naphthalene LC-MS: m/z 324 (M+H); RT=1.43 min/2.5 min $^1$H NMR (400 MHz, $d_6$-DMSO): δ=8.76 (s, 1H), 7.36 (d, J=4.8 Hz, 1H), 7.55 (d, J=4.8 Hz, 1H), 7.32 (dd, J=11.6, 2.4 Hz, 1H), 6.75 (dd, J=11.6, 2.4 Hz, 1H), 4.50 (s, 3 H), 4.15 (s, 3 H), 2.20 (s, 3 H).

Example 14

7,8-Dimethoxy-3-methyl-1-(3,5-dimethoxyphenyl)-3H-2,3,4,5-tetraazacyclopenta[a]naphthalene LC-MS: m/z 381 (M+H); RT=1.63 min/2.5 min $^1$H NMR (400 MHz, CDCl$_3$): δ=8.02 (s, 2H), 7.71 (s, 1H), 7.00 (s, 1 H), 6.61 (s, 1 H), 4.52 (s, 3 H), 4.12 (s, 3 H), 3.93 (s, 3 H), 3.88 (s, 6 H).

Example 15

1-Hydroxy-6-fluoro-8-methoxy-3-methyl-3H-2,3,4,5-tetraazacyclopenta[a]naphthalene LC-MS: m/z 261 (M+H); RT=1.39 min/2.5 min $^1$H NMR (400 MHz, $d_6$-DMSO): δ=11.78 (brs, 1H), 7.36 (d, J=2.4 Hz, 1H), 7.28 (dd, J=11.6, 2.4 Hz, 1H), 4.18 (s, 3 H), 4.01 (s, 3 H).

Example 16

6-Fluoro-8-methoxy-3-methyl-1-morpholin-4-yl-3H-2,3,4,5-tetraazacyclopenta[a]naphthalene

Example 17

6-fluoro-8-methoxy-3-methyl-1-(2-chlorophenyl)-3H-2,3,4,5-tetraazacyclopenta[a]naphthalene

ESI-MS: [M+H$^+$]=343.10

Example 18

1-Cyclopropyl-6-fluoro-8-methoxy-3-methyl-3H-2,3,4,5-tetraazacyclopenta[a]naphthalene ESI-MS: [2M+Na$^+$]=567.10, [M+H$^+$]=273.10;
$^1$H NMR (CDCl$_3$, 600 MHz): δ=7.57 (s, 1 H), 7.08 (d, 1 H), 4.40 (s, 3 H), 4.05 (s, 3 H), 2.36 (m sym., 1 H), 1.15 (m, 4 H).

Example 19

7,8-dimethoxy-1,3-dimethyl-3H-2,3,4,5-tetraazacyclopenta[a]naphthalene $^1$H NMR (CDCl$_3$, 600 MHz): δ=8.03 (s, 1 H), 7.49 (s, 1 H), 4.40 (s, 3 H), 4.14 (d, 6 H), 2.89 (s, 3 H).

Example 20

1,6,8-trimethoxy-3-methyl-pyrazolo[3,4-c]cinnoline

ESI-MS: [2M+Na$^+$]=571.20, [M+H$^+$]=275.10;
$^1$H NMR (CDCl$_3$, 600 MHz): δ=7.12 (s, 1 H), 6.62 (s, 1 H), 4.28 (s, 3 H), 4.20 (s, 3 H), 4.13 (s, 3 H), 4.03 (s, 3 H).

Example 21

1-isobutyl-6,8-dimethoxy-3-methyl-pyrazolo[3,4-c]cinnoline $^1$H NMR (CD$_3$OD, 600 MHz): δ=7.10 (s, 1 H), 6.85 (s, 1 H), 4.35 (s, 2 H), 4.13 (s, 3 H), 4.06 (s, 3 H), 3.11 (d, 2 H), 2.66 (s, 1 H), 2.21 (sept., 1 H), 1.07 (m sym, 6 H).

Example 22

1-cyclopropyl-6,8-dimethoxy-3-methyl-pyrazolo[3,4-c]cinnoline $^1$H NMR (CD$_3$OD, 600 MHz): δ=7.38 (s, 1 H), 6.81 (s, 1 H), 4.29 (s, 3 H), 4.13 (s, 3 H), 4.05 (s, 3 H), 2.45 (sept., 1 H), 1.18 (m sym., 3 H), 1.05 (m sym., 3 H).

Example 23

7,8-Dimethoxy-1-methyl-3H-2,3,4,5-tetraaza-cyclopenta[a]

Example 24

8-Fluoro-6-methoxy-3-methyl-3H-2,3,4,5-tetraaza-cyclopenta[a]naphthalene

LC-MS (Method B): m/z 233 (M+H) RT=1.51 min/2.5 min $^1$H NMR (400 MHz, d$_6$-DMSO): δ=8.76 (s, 1H), 7.83~7.80 (m, 1H), 7.30~7.26 (m, 1H), 4.42 (s, 3 H), 4.14 (s, 3 H).

Example 25

5-(6,8-Dimethoxy-3-methyl-pyrazolo[3,4-c]cinnolin-1-yl)-2,4-dimethyl-thiazole

ESI-MS: [M+H]$^+$=356.10

Example 26

3-(6,8-dimethoxy-3-methyl-pyrazolo[3,4-c]cinnolin-1-yl)benzamide $^1$H NMR (methanol-d$_4$, 600 MHz): δ=8.44 (s, 1H), 8.05 (t, 2H), 7.72 (t, 1H), 7.14 (d, 1H), 6.86 (d, 1H), 4.48 (s, 3H), 4.13 (s, 3H), 3.82 (s, 3H)

II. Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM MgCl$_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29° C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, IC$_{50}$ value of inhibitor can be obtained by plotting inhibitor concentration against PDE activity at that concentration. The results are shown in Table 1.

TABLE 1

| Example | IC$_{50}$ |
| --- | --- |
| 5 | +++ |
| 6 | +++ |
| 8 | +++ |
| 9 | +++ |
| 11 | + |
| 13 | +++ |
| 14 | + |
| 17 | + |
| 19 | ++ |
| 20 | ++ |
| 23 | +++ |

TABLE 1-continued

| Example | IC$_{50}$ |
|---------|-----------|

1) +++: IC$_{50}$ < 100 nM ++: 100 nM ≤ IC$_{50}$ ≤ 200 nM +: 200 nM < IC$_{50}$ < 500 nM b) Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/ (content of microsomal protein in mg/ml)×1000 [ml/min/mg] (modified from references: Di, The Society for Biomolecular Screening, 2003, 453-462; Obach, DMD, 1999 vol 27. N 11, 1350-1359). The results are shown in Table 2.

TABLE 2

| Ex. | Rat mCl[2] [µl min$^{-1}$ mg$^{-1}$] | Human mCl[2] [µl min$^{-1}$ mg$^{-1}$] |
|-----|--------------------------------------|----------------------------------------|
| 10  | ++                                   | ++                                     |
| 11  | ++                                   | ++                                     |
| 12  | ++                                   | ++                                     |
| 13  | ++                                   | ++                                     |
| 14  | o                                    | ++                                     |
| 15  | ++                                   | ++                                     |
| 17  | o                                    | ++                                     |
| 19  | ++                                   | +                                      |
| 20  | ++                                   | ++                                     |
| 23  | +                                    | ++                                     |

Ex. Example
mCl microsomal clearance
[2]++: <100 µl min$^{-1}$ mg$^{-1}$ +: 100-220 µl min$^{-1}$ mg$^{-1}$ o: >220 µl min$^{-1}$ mg$^{-1}$

We claim:

1. Compound of formula I

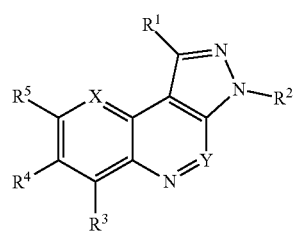

(I)

where:

X is C—R$^6$ or N;

Y is N;

R$^1$ is selected from the group consisting of hydrogen, halogen, cyano, nitro, R$^{11}$, OH, OR$^{12}$, S(O)$_q$R$^{13}$, C(O)H, C(O)R$^{14}$, C(O)OH, C(O)OR$^{15}$, OC(O)R$^{16}$, Y$^1$—NR$^{17}$R$^{18}$, Y$^1$—N(R$^{19}$)—Y$^3$—NR$^{17}$R$^{18}$, Y$^1$—N(R$^{19}$)—Y$^2$—R$^{15a}$ and a moiety Z$^1$—Ar$^1$;

R$^2$ is selected from the group consisting of R$^{21}$, OR$^{22}$, C(O)R$^{23}$, C(O)OR$^{24}$, Y$^1$—NR$^{25}$R$^{26}$, Y$^1$—N(R$^{27}$)—Y$^3$—NR$^{25}$R$^{26}$, Y$^1$—N(R$^{27}$)—Y$^2$—R$^{28}$ and a moiety Z$^2$—Ar$^2$, R$^2$ may also be hydrogen, if R$^1$ is different from hydrogen and OH or if R$^3$ is different from hydrogen;

R$^3$ is selected from the group consisting of hydrogen, halogen, cyano, nitro, R$^{31}$, OR$^{32}$, S(O)$_q$R$^{33}$, C(O)H, C(O)R$^{34}$, C(O)OH, C(O)OR$^{35}$, OC(O)R$^{36}$, Y$^1$—NR$^{37}$R$^{38}$, Y$^1$—N(R$^{39}$)—Y$^3$—NR$^{37}$R$^{38}$, Y$^1$—N(R$^{39}$)—Y$^2$—R$^{35a}$, and Z$^3$—Ar$^3$;

R$^4$ is selected from the group consisting of hydrogen, halogen, cyano, nitro, R$^{41}$, OR$^{42}$, S(O)$_q$R$^{43}$, C(O)H, C(O)R$^{44}$, C(O)OH, C(O)OR$^{45}$, OC(O)R$^{46}$, Y$^1$—NR$^{47}$R$^{48}$, Y$^1$—N(R$^{49}$)—Y$^3$—NR$^{47}$R$^{48}$, Y$^1$—N(R$^{49}$)—Y$^2$—R$^{45a}$, and Z$^4$—Ar$^4$;

R$^5$ is selected from the group consisting of hydrogen, halogen, cyano, nitro, R$^{51}$, OR$^{52}$, S(O)$_q$R$^{53}$, C(O)H, C(O)R$^{54}$, C(O)OH, C(O)OR$^{55}$, OC(O)R$^{56}$, Y$^1$—NR$^{57}$R$^{58}$, Y$^1$—N(R$^{59}$)—Y$^3$—NR$^{57}$R$^{58}$, Y$^1$—N(R$^{59}$)—Y$^2$—R$^{55a}$, and Z$^5$—Ar$^5$;

or

R$^4$ and R$^5$, together with the carbon atoms, to which they are attached, may form a fused 5-, 6- or 7-membered carbocyclic or heterocyclic ring, where the fused carbocyclic or heterocyclic ring may be saturated, partially unsaturated or aromatic and where the heterocyclic ring may have 1, 2 or 3 heteroatom moieties as ring members, which are selected from the group consisting of O, N, S, S(O), S(O)$_2$ or N—R$^x$ and where the carbocyclic or heterocyclic ring is unsubstituted or may carry 1, 2, 3 or 4 radicals R$^{yy}$;

R$^6$ is selected from the group consisting of hydrogen, halogen, cyano, nitro, R$^{61}$, OR$^{62}$, S(O)$_q$R$^{63}$, C(O)H, C(O)R$^{64}$, C(O)OH, C(O)OR$^{65}$, OC(O)R$^{66}$, Y$^1$—NR$^{67}$R$^{68}$, Y$^1$—N(R$^{69}$)—Y$^3$—NR$^{67}$R$^{68}$ and Y$^1$—N(R$^{69}$)—Y$^2$—R$^{65a}$;

R$^{11}$, R$^{12}$, R$^{13}$, R$^{14}$, R$^{15}$, R$^{16}$, R$^{21}$, R$^{22}$, R$^{23}$, R$^{24}$, R$^{31}$, R$^{32}$, R$^{33}$, R$^{34}$, R$^{35}$, R$^{36}$, R$^{41}$, R$^{42}$, R$^{43}$, R$^{44}$, R$^{45}$, R$^{46}$, R$^{51}$, R$^{52}$, R$^{53}$, R$^{54}$, R$^{55}$, R$^{56}$, R$^{61}$, R$^{62}$, R$^{63}$, R$^{64}$, R$^{65}$, and R$^{66}$, independently of each other, are selected from the group consisting of tri-C$_1$-C$_4$-alkylsilyl, C$_1$-C$_8$-alkyl, C$_2$-C$_8$-alkenyl, C$_2$-C$_8$-alkynyl, C$_3$-C$_8$-cycloalkyl, C$_5$-C$_8$-cycloalkenyl, C$_3$-C$_8$-cycloalkyl-C$_1$-C$_4$-alkyl, where the 6 aforementioned substituents may be unsubstituted, partially or completely halogenated or carry 1, 2 or 3 radicals R$^y$, and C-bound 5- to 8-membered heterocyclyl, which is saturated or partially unsaturated and has 1 or 2 heteroatom moieties as ring members, which are selected from the group consisting of O, N, S, S(O), S(O)$_2$ or N—R$^x$, where heterocyclyl is unsubstituted or carries 1, 2, 3 or 4 radicals R$^{yy}$;

R$^{17}$ and R$^{18}$, independently of each other, are selected from the group consisting of tri-C$_1$-C$_4$-alkylsilyl, C$_1$-C$_8$-alkyl, C$_2$-C$_8$-alkenyl, C$_2$-C$_8$-alkynyl, C$_3$-C$_8$-cycloalkyl, C$_5$-C$_8$-cycloalkenyl, C$_3$-C$_8$-cycloalkyl-C$_1$-C$_4$-alkyl, where the 6 aforementioned substituents may be unsubstituted, partially or completely halogenated or carry 1, 2 or 3 radicals R$^y$, C$_1$-C$_8$-alkylcarbonyl, C$_1$-C$_4$-haloalkylcarbonyl, C$_1$-C$_8$-alkylsulfonyl, C$_1$-C$_4$-haloalkylsulfonyl, and C-bound 5- to 8-membered heterocyclyl, which is saturated or partially unsaturated and has 1 or 2 heteroatom moieties as ring members, which are selected from the group consisting of O, N, S, S(O), S(O)$_2$ and N—R$^x$, where heterocyclyl is unsubstituted or carries 1, 2, 3 or 4 radicals R$^{yy}$ or R$^{17}$ and R$^{18}$, together with the nitrogen atom, to which they are attached, form an N-bound 5- to 8-membered heterocyclyl, which is saturated, partially unsaturated or aromatic and in addition to the nitrogen atom may have 1 or 2 further heteroatom moieties as ring members, which are selected from the group consisting of O, N, S, S(O), S(O)$_2$ and N—R$^x$, where heterocyclyl is unsubstituted or carries 1, 2, 3 or 4 radicals R$^{yy}$;

R$^{19}$, R$^{27}$, R$^{39}$, R$^{49}$, R$^{59}$ and R$^{69}$, independently of each other, are hydrogen or have one of the meanings given for R$^{11}$;

R$^{25}$ and R$^{26}$ are as defined for R$^{17}$ and R$^{18}$;
R$^{37}$ and R$^{38}$ are as defined for R$^{17}$ and R$^{18}$;
R$^{47}$ and R$^{48}$ are as defined for R$^{17}$ and R$^{18}$;
R$^{57}$ and R$^{58}$ are as defined for R$^{17}$ and R$^{18}$;
R$^{67}$ and R$^{68}$ are as defined for R$^{17}$ and R$^{18}$;
R$^{15a}$, R$^{28}$, R$^{35a}$, R$^{45a}$, R$^{55a}$ and R$^{65a}$, independently of each other, have one of the meanings given for R$^{11}$;

q is 0, 1 or 2

Ar$^1$, Ar$^2$, Ar$^3$, Ar$^4$, Ar$^5$, and Ar$^6$, independently of each other, are selected from the group consisting of aryl, monocyclic 5- or 6-membered hetaryl and bicyclic 9 or 10 membered hetaryl, where hetaryl has 1, 2 or 3 heteroatoms as ring members which are selected from O, S and N, where aryl and hetaryl are unsubstituted or may carry 1, 2, 3 or 4 identical or different substituents R$^{Ar}$;

Y$^1$ is a single bond, C$_1$-C$_4$-alkylene, Y$^5$—O—Y$^6$, Y$^5$—S(O)$_q$—Y$^6$, Y$^5$—C(O)—Y$^6$, Y$^5$—C(S)—Y$^6$, Y$^5$—C(O)O—Y$^6$, Y$^5$—OC(O)—Y$^6$, or Y$^5$—N(R$^z$)—Y$^4$;

Y$^2$ is a single bond, C$_1$-C$_4$-alkylene, Y$^5$—O—Y$^6$, Y$^5$—S(O)$_q$—Y$^6$, Y$^5$—C(O)—Y$^6$, Y$^5$—C(S)—Y$^6$, Y$^5$—C(O)O—Y$^6$, Y$^5$—OC(O)—Y$^6$, or Y$^5$—N(R$^z$)—Y$^4$;

Y$^3$ is a single bond, C$_1$-C$_4$-alkylene, Y$^5$—S(O)$_q$—Y$^6$, Y$^5$—C(O)—Y$^6$, Y$^5$—C(S)—Y$^6$, Y$^5$—C(O)O—Y$^6$, or Y$^5$—OC(O)—Y$^6$;

Y$^4$ is a C$_1$-C$_4$-alkylene, Y$^5$—S(O)$_q$—Y$^6$, Y$^5$—C(O)—Y$^6$, Y$^5$—C(S)—Y$^6$, Y$^5$—C(O)O—Y$^6$, or Y$^5$—OC(O)—Y$^6$;

Y$^5$ is a single bond or C$_1$-C$_4$-alkylene;
Y$^6$ is a single bond or C$_1$-C$_4$-alkylene;

Z$^1$ is a single bond, C$_1$-C$_4$-alkylene, Y$^5$—O—Y$^6$, Y$^5$—S(O)$_q$—Y$^6$, Y$^5$—C(O)—Y$^6$, Y$^5$—C(S)—Y$^6$, Y$^5$—C(O)O—Y$^6$, Y$^5$—OC(O)—Y$^6$, or Y$^5$—N(R$^z$)—Y$^4$;

Z$^2$ is a single bond, C$_1$-C$_4$-alkylene, Y$^5$—O—Y$^6$, Y$^5$—C(O)—Y$^6$, Y$^5$—C(S)—Y$^6$, Y$^5$—C(O)O—Y$^6$, Y$^5$—OC(O)—Y$^6$, or Y$^5$—N(R$^z$)—Y$^4$;

Z$^3$, Z$^4$, Z$^5$, and Z$^6$ are independently of each other selected from the group consisting of a single bond, C$_1$-C$_4$-alkylene, Y$^5$—O—Y$^6$, Y$^5$—S(O)$_q$—Y$^6$, Y$^5$—C(O)—Y$^6$, Y$^5$—C(S)—Y$^6$, Y$^5$—C(O)O—Y$^6$, Y$^5$—OC(O)—Y$^6$ and Y$^5$—N(R$^z$)—Y$^4$;

R$^x$ is selected from the group consisting of hydrogen, C$_1$-C$_8$-alkyl, C$_2$-C$_8$-alkenyl, C$_2$-C$_8$-alkynyl, C$_3$-C$_8$-cycloalkyl, C$_5$-C$_8$-cycloalkenyl, C$_3$-C$_8$-cycloalkyl-C$_1$-C$_4$-alkyl, where the 6 aforementioned substituents may be unsubstituted, partially or completely halogenated or carry 1, 2 or 3 radicals R$^y$, phenyl and phenyl-C$_1$-C$_4$-alkyl, where phenyl and phenyl-C$_1$-C$_4$-alkyl are unsubstituted or may carry 1, 2, 3 or 4 radicals R$^{yy}$;

R$^y$ is selected from the group consisting of cyano, OH, C$_1$-C$_4$-alkyl, C$_1$-C$_4$-haloalkyl, OR$^{y2}$, S(O)$_q$R$^{y3}$, C(O)H, C(O)R$^{y4}$, C(O)OH, C(O)OR$^{y5}$, OC(O)R$^{y6}$, Y$^1$—NR$^{y7}$R$^{y8}$, Y$^1$—N(R$^{y9}$)—Y$^3$—NR$^{y7}$R$^{y8}$ and Y$^1$—N(R$^{y9}$)—Y$^2$—R$^{y0}$;

R$^{yy}$ is selected from the group consisting of cyano, halogen, R$^{y1}$, OH, OR$^{y2}$, S(O)$_q$R$^{y3}$, C(O)H, C(O)R$^{y4}$, C(O)OH, C(O)OR$^{y5}$, OC(O)R$^{y6}$, Y$^1$—NR$^{y7}$R$^{y8}$, Y$^1$—N(R$^{y9}$)—Y$^3$—NR$^{y7}$R$^{y8}$ and Y$^1$—N(R$^{y9}$)—Y$^2$—R$^{y0}$;

R$^{y0}$, R$^{y1}$, R$^{y2}$, R$^{y3}$, R$^{y4}$, R$^{y5}$ and R$^{y6}$, independently of each other, are selected from the group consisting of C$_1$-C$_8$-alkyl, C$_2$-C$_8$-alkenyl, C$_2$-C$_8$-alkynyl, C$_3$-C$_8$-cycloalkyl, C$_5$-C$_8$-cycloalkenyl, C$_3$-C$_8$-cycloalkyl-C$_1$-C$_4$-alkyl, and C-bound 5- to 8-membered heterocyclyl, which is saturated or partially unsaturated and has 1 or 2 heteroatom moieties as ring members, which are selected from the group consisting of O, N, S, S(O), S(O)$_2$, NH or N—(C$_1$-C$_4$-alkyl);

R$^{y7}$ and R$^{y8}$ are as defined for R$^{y0}$ or, together with the nitrogen atom, to which they are attached, form an N-bound 5- to 8-membered heterocyclyl, which is saturated or partially unsaturated and in addition to the nitrogen atom may have 1 or 2 further heteroatom moieties as ring members, which are selected from the group consisting of O, N, S, S(O), S(O)$_2$, NH and N—(C$_1$-C$_4$-alkyl), where heterocyclyl is unsubstituted or carries 1, 2, 3 or 4 radicals selected from C$_1$-C$_4$-alkyl;

R$^{y9}$ is hydrogen or has one of the meanings given for R$^{y0}$;

R$^{Ar}$ is selected from the group consisting of halogen, cyano, nitro, OH, C(O)NH$_2$, R$^{Ar1}$, OR$^{Ar2}$, S(O)$_q$R$^{Ar3}$, C(O)H, C(O)R$^{Ar4}$, C(O)OH, C(O)OR$^{Ar5}$, OC(O)R$^{Ar6}$, Y$^1$—NR$^{Ar7}$R$^{Ar8}$, Y$^1$—N(R$^{Ar9}$)—Y$^3$—NR$^{Ar7}$R$^{Ar8}$, and Y$^1$—N(R$^{Ar9}$)—Y$^2$—R$^{Ar0}$, where R$^{Ar0}$, R$^{Ar1}$, R$^{Ar2}$, R$^{Ar3}$, R$^{Ar4}$, R$^{Ar5}$ and R$^{Ar6}$ have one of the meanings given for R$^{11}$ or may be phenyl, R$^{Ar7}$ and R$^{Ar8}$ are as defined for R$^{17}$ and R$^{18}$, and R$^{Ar9}$ has one of the meanings given for R$^{19}$;

R$^z$ has one of the meanings given for R$^x$;

or an N-oxides, tautomers, or pharmaceutically acceptable salts thereof;

except for the compounds of the formula I belonging to the following groups a), b), c), and d), where group a): compounds of the formula I, where X is CH, Y is N, R$^1$ is methyl, R$^2$ is Hydrogen phenyl, benzyl or benzoyl, R$^3$ is hydrogen, R$^4$ and R$^5$ are methoxy, and pharmaceutically acceptable salts thereof;

group b): compounds of the formula I, where X is CH, Y is N, R$^1$ is phenyl, R$^2$ is phenyl, R$^3$ is hydrogen, R$^4$ and R$^5$ are methoxy, and pharmaceutically acceptable salts thereof;

group c): compounds of the formula I, where X is CH, Y is N, R$^1$ is 4-chlorophenyl, R$^2$ is 3,5-dichloro-2-pyridyl, R$^3$ is hydrogen, R$^4$ and R$^5$ are methoxy, and pharmaceutically acceptable salts thereof, group d): compounds of the formula I, where X is CH, Y is N, R$^1$ is methyl, ethyl, benzyl or phenyl, R$^2$ is hydrogen, R$^3$ is hydrogen, R$^4$ and R$^5$ are both methoxy and the compound of the formula I, where X is CH, Y is N, R$^1$ is methyl, R$^2$ is hydrogen, R$^3$ is hydrogen, R$^4$ is methoxy and R$^5$ is hydrogen, and the pharmaceutically acceptable salts thereof.

2. The compound of claim 1, where X is C—R$^6$.

3. The compound of claim 2, where R$^6$ is hydrogen, halogen, methyl, methoxy, CHF$_2$, CF$_3$, OCHF$_2$ or OCF$_3$.

4. The compound of claim 1, where X is N.

5. The compound of claim 1, where R$^1$ is a radical CN, R$^{11}$, a moiety Y$^1$—NR$^{17}$R$^{18}$ or a moiety Z$^1$—Ar$^1$.

6. The compound of claim 5, where R$^1$ is a moiety Z$^1$—Ar$^1$, where Z$^1$ is a single bond.

7. The compound of any of claim 5, where R$^1$ is a moiety Z$^1$—Ar$^1$, where Ar$^1$ is selected from the group consisting of phenyl, thienyl, pyrazolyl, isoxazolyl, thiazolyl, 1,2,4-oxadiazolyl and pyridyl, where phenyl, thienyl, pyrazolyl, isoxazolyl, thiazolyl, 1,2,4-oxadiazolyl and pyridyl are unsubstituted or carry 1, 2, 3 or 4 identical or different substituents R$^{Ar}$.

8. The compound of any of the preceding claim 1, where R$^2$ is a radical R$^{21}$ which is selected From the group consisting of trimethylsilyl, C$_1$-C$_8$-alkyl, C$_3$-C$_8$-cycloalkyl and C$_3$-C$_8$-cycloalkyl-C$_1$-C$_{-4}$-alkyl, where the three last mentioned radicals may be unsubstituted, partially or completely halogenated or where the C$_3$-C$_8$-cycloalkyl radicals may carry 1, 2 or 3 methyl groups.

9. The compound of claim 1, where one or two of the radicals R$^3$, R$^4$, R$^5$ and R$^6$ are different from hydrogen.

10. The compound of claim 9, where R$^5$ is different from hydrogen and one of R$^3$ and R$^4$ is different from hydrogen.

11. The compound of claim 1, where R$^3$ is selected from the group consisting of hydrogen, halogen and OR$^{32}$.

12. The compound as claimed in claim 1, where R$^4$ is selected from the group consisting of hydrogen, halogen, OR$^{42}$ and a group Z$^4$—Ar$^4$.

13. The compound of claim 1, where R$^5$ is selected from the group consisting of hydrogen, halogen, OR$^{52}$, a group Y$^1$—NR$^{57}$R$^{58}$ and a group Z$^5$—Ar$^5$.

14. The compound of claim 1, wherein R$^4$ and R$^5$, together with the carbon atoms, to which they are attached, form a fused 5-, 6- or 7-membered saturated heterocyclic ring, where the fused heterocyclic ring has 1 or 2 oxygen atoms as ring members and where the fused heterocyclic ring is unsubstituted or may carry 1 or 2 radicals selected from methyl, methoxy and fluorine.

15. The compound of claim 1, where:
R$^3$ is methoxy, difluoromethoxy, trifluoromethoxy, 2,2-difluoroethoxy or 2,2,2-trifluoroethoxy,
R$^4$ is hydrogen and
R$^5$ is fluorine, chlorine, methoxy, difluoromethoxy, trifluoromethoxy, 2,2-difluoroethoxy or 2,2,2-trifluoroethoxy,
or
R$^3$ is hydrogen,
R$^4$ is fluorine, chlorine, methoxy, difluoromethoxy, trifluoromethoxy, 2,2-difluoroethoxy or 2,2,2-trifluoroethoxy and
R$^5$ is fluorine, chlorine, methoxy, difluoromethoxy, trifluoromethoxy, 2,2-difluoroethoxy or 2,2,2-trifluoroethoxy, provided that at least one of the radicals R$^4$ and R$^5$ is methoxy, difluoromethoxy, trifluoromethoxy, 2,2-difluoroethoxy or 2,2,2-trifluoroethoxy;
or
R$^5$ is hydrogen,
R$^4$ is fluorine, chlorine methoxy, difluoromethoxy, trifluoromethoxy, 2,2-difluoroethoxy or 2,2,2-trifluoroethoxy and
R$^3$ is fluorine, chlorine methoxy, difluoromethoxy, trifluoromethoxy, 2,2-difluoroethoxy or 2,2,2-trifluoroethoxy, provided that at least one of the radicals R$^3$ and R$^5$ is methoxy, difluoromethoxy, trifluoromethoxy, 2,2-difluoroethoxy or 2,2,2-trifluoroethoxy;
or
R$^3$ is hydrogen, and
R$^4$ and R$^5$ together form in particular a moiety OCH$_2$O or OCF$_2$O;
or
R$^3$ and R$^4$ are hydrogen, and
R$^5$ is selected from the group consisting of fluorine, chlorine, C$_1$-C$_4$-alkoxy, C$_1$-C$_4$-haloalkoxy, the moiety NR$^{57}$R$^{58}$ and the moiety Z$^5$—Ar$^5$.

16. The compound of claim 1 which is a compound of the formula I-A

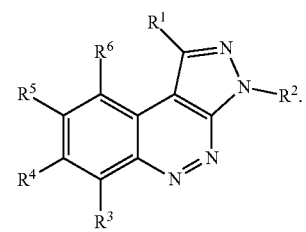

(I-A)

17. The compound of claim 1 which is a compound of the formula I-B

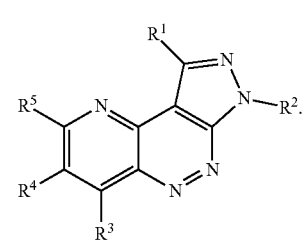

(I-B)

18. The compound of claim 1, which is selected from the group consisting of:
6,8-difluoro-3-methyl-1-(2-methylpyridine-3-yl)-3H-2,3,4,5-tetraazacyclopenta[a]naphthalene;
6,8-difluoro-3-methyl-1-(2-chlorophenyl)-3H-2,3,4,5-tetraazacyclopenta[a]naphthalene;
6,8-dimethoxy-3-methyl-1-(2-methylpyridine-3-yl)-3H-2,3,4,5-tetraazacyclopenta[a]naphthalene;
1-hydroxy-6,8-dimethoxy-3-methyl-3H-2,3,4,5-tetraazacyclopenta[a]naphthalene;
6,8-dimethoxy-3-methyl-1-(2-chlorophenyl)-3H-2,3,4,5-tetraazacyclopenta[a]naphthalene;
8-fluoro-6-methoxy-3-methyl-1-(3-methylpyridine-4-yl)-3H-2,3,4,5-tetraazacyclopenta[a]naphthalene;
8-fluoro-6-methoxy-3-methyl-1-(2-methylpyridine-3-yl)-3H-2,3,4,5-tetraazacyclopenta[a]naphthalene;
8-fluoro-6-methoxy-3-methyl-1-(2-chlorophenyl)-3H-2,3,4,5-tetraazacyclopenta[a]naphthalene;
8-fluoro-6-methoxy-3-methyl-3H-2,3,4,5-tetraazacyclopenta[a]naphthalene;
6-fluoro-8-methoxy-3-methyl-1-(3-methylpyridine-4-yl)-3H-2,3,4,5-tetraazacyclopenta[a]naphthalene;
6-fluoro-8-methoxy-3-methyl-1-(2-chlorophenyl)-3H-2,3,4,5-tetraazacyclopenta[a]naphthalene;
1-hydroxy-6-fluoro-8-methoxy-3-methyl-3H-2,3,4,5-tetraazacyclopenta[a]naphthalene;

6-fluoro-8-methoxy-3-methyl-1-morpholin-4-yl-3H-2,3,4,5-tetraazacyclopenta[a]naphthalene;

7,8-dimethoxy-1,3-dimethyl-3H-2,3,4,5-tetraazacyclopenta[a]naphthalene;

7,8-dimethoxy-3-methyl-1-(3,5-dimethoxyphenyl)-3H-2,3,4,5-tetraazacyclopenta[a]naphthalene;

7,8-dimethoxy-3-methyl-1-(5-methylpyridine-3-yl)-3H-2,3,4,5-tetraazacyclopenta[a]naphthalene;

1-hydroxy-7,8-dimethoxy-3-methyl-3H-2,3,4,5-tetraazacyclopenta[a]naphthalene;

1-cyclopropyl-6-fluoro-8-methoxy-3-methyl-3H-2,3,4,5-tetraazacyclopenta[a]naphthalene;

1,6,8-trimethoxy-3-methyl-pyrazolo[3,4-c]cinnoline;

1-isobutyl-6,8-dimethoxy-3-methyl-pyrazolo[3,4-c]cinnoline;

1-cyclopropyl-6,8-dimethoxy-3-methyl-pyrazolo[3,4-c]cinnoline;

7,8-dimethoxy-1-methyl-3H-2,3,4,5-tetraaza-cyclopenta[a]naphthalene; and 8-fluoro-6-methoxy-3-methyl-3H-2,3,4,5-tetraaza-cyclopenta[a]naphthalene;

or an N-oxides, tautomers, or pharmaceutically acceptable salts thereof.

19. The compound of claim 1, which is selected from the group consisting of:

5-(6,8-dimethoxy-3-methyl-pyrazolo[3,4-c]cinnolin-1-yl)-2,4-dimethyl-thiazole; and 3-(6,8-dimethoxy-3-methyl-pyrazolo[3,4-c]cinnolin-1-yl)benzamide;

or an N-oxides, tautomers, or pharmaceutically acceptable salts thereof.

20. The compound of claim 1, where $R^2$ is methy.

21. The compound of claim 1, where $R^1$ is a moiety $Z^1$—$Ar^1$, where $Z^1$ is a single bond, and where $R^2$ is a radical $R^{21}$ which is selected from the group consisting of trimethylsilyl, $C_1$-$C_8$-alkyl, $C_3$-$C_8$-cycloalkyl and $C_3$-$C_8$-cycloalkyl-$C_1$-$C_4$-alkyl, where the three last mentioned radicals may be unsubstituted, partially or completely halogenated or where the $C_3C_8$-cycloalkyl radicals may carry 1, 2 or 3 methyl groups.

22. The compound of claim 1, where $R^1$ is a moiety $Z^1$—$Ar^1$, where $Z^1$ is a single bond, and where $R^2$ is methyl.

23. A Pharmaceutical composition which comprises a pharmaceutically acceptable carrier and a compound of claim 1.

24. A method for treating a disorder selected from the group consisting of schizophrenia, depression, bipolar disorder, cognitive dysfunction associated with schizophrenia, cognitive dysfunction associated with Alzheimer's disease, Huntington's disease, substance-related disorder, and diet-induced obesity, said method comprising administering an effective amount of at least one compound of claim 1 to a mammal in need thereof.

25. The method of claim 24, where the disorder is schizophrenia.

26. The method of claim 24, where the disorder is a cognitive dysfunction associated with schizophrenia.

27. The method of claim 24, where the disorder is a bipolar disorder.

28. The method of claim 24, where the disorder is a depression.

29. The method of claim 24, where the disorder is a dysfunction associated with Alzheimer's disease.

30. The method of claim 24, where the disorder is a diet-induced obesity.

31. The method of claim 24, wherein the disorder is a substance-related disorder.

32. The method of claim 24, wherein the disorder is Huntington's disease.

33. The method of claim 31, wherein the substance-related disorder is substance abuse.

* * * * *